(12) United States Patent
Beaudoin et al.

(10) Patent No.: US 8,853,250 B2
(45) Date of Patent: Oct. 7, 2014

(54) SODIUM CHANNEL INHIBITORS

(75) Inventors: Serge Beaudoin, Cary, NC (US); Matthew Scott Johnson, Durham, NC (US); Brain Edward Marron, Durham, NC (US); Mark J. Suto, Chapel Hill, NC (US)

(73) Assignee: Icagen, Inc., Durham, NC (US)

( * ) Notice: Subject to any disclaimer, the term of this patent is extended or adjusted under 35 U.S.C. 154(b) by 943 days.

(21) Appl. No.: 12/669,018

(22) PCT Filed: Jul. 14, 2008

(86) PCT No.: PCT/US2008/070018
§ 371 (c)(1),
(2), (4) Date: Jun. 25, 2010

(87) PCT Pub. No.: WO2009/012241
PCT Pub. Date: Jan. 22, 2009

(65) Prior Publication Data
US 2010/0267782 A1    Oct. 21, 2010

Related U.S. Application Data

(60) Provisional application No. 60/949,588, filed on Jul. 13, 2007.

(51) Int. Cl.
*A01N 43/78* (2006.01)
*A61K 31/425* (2006.01)
*C07D 277/52* (2006.01)

(52) U.S. Cl.
CPC .................................. *C07D 277/52* (2013.01)
USPC .......................................... 514/370; 548/197

(58) Field of Classification Search
USPC ................. 514/370, 183; 546/270.4; 548/197
See application file for complete search history.

(56) References Cited

U.S. PATENT DOCUMENTS

| 5,591,761 | A | 1/1997 | Chan et al. |
| 2006/0138400 | A1 | 6/2006 | Saso et al. |
| 2006/0276464 | A1* | 12/2006 | Gopalsamy et al. ....... 514/230.5 |
| 2007/0135493 | A1 | 6/2007 | Wang et al. |
| 2007/0161821 | A1 | 7/2007 | Hall et al. |

FOREIGN PATENT DOCUMENTS

| EP | 1655469 | 10/2006 |
| WO | WO03037274 | 5/2003 |
| WO | 2004014300 | 2/2004 |
| WO | 2004103980 | 12/2004 |
| WO | WO 2004112784 | * 12/2004 |
| WO | WO2007021941 | 2/2007 |

* cited by examiner

*Primary Examiner* — Uma Ramachandran
(74) *Attorney, Agent, or Firm* — Richard V. Zanzalari

(57) ABSTRACT

Compounds, compositions and methods are provided which are useful in the treatment of diseases through the inhibition of sodium ion flux through voltage-gated sodium channels. More particularly, the invention provides substituted aryl sulfonamides, compositions comprising these compounds, as well as methods of using these compounds or compositions in the treatment of central or peripheral nervous system disorders, particularly pain and chronic pain by blocking sodium channels associated with the onset or recurrence of the indicated conditions. The compounds, compositions and methods of the present invention are of particular use for treating neuropathic or inflammatory pain by the inhibition of ion flux through a voltage-gated sodium channel.

3 Claims, No Drawings

SODIUM CHANNEL INHIBITORS

This application claims priority to U.S. Provisional Patent Application No. 60/949,588 filed Jul. 13, 2007, which application is incorporated herein by reference in its entirety and for all purposes.

This invention relates to the use of certain compounds as sodium channel blockers and to the treatment of pain by the inhibition of sodium channels. Additionally, this invention relates to novel compounds that are useful as sodium channel blockers.

BACKGROUND OF THE INVENTION

Voltage-gated sodium channels are found in all excitable cells including myocytes of muscle and neurons of the central and peripheral nervous system. In neuronal cells sodium channels are primarily responsible for generating the rapid upstroke of the action potential. In this manner sodium channels are essential to the initiation and propagation of electrical signals in the nervous system. Proper and appropriate function of sodium channels is therefore necessary for normal function of the neuron. Consequently, aberrant sodium channel function is thought to underlie a variety of medical disorders (See Hubner C A, Jentsch T J, *Hum. Mol. Genet.*, 11(20): 2435-45 (2002) for a general review of inherited ion channel disorders) including epilepsy (Yogeeswari et al., *Curr. Drug Targets*, 5(7): 589-602 (2004)), arrhythmia (Noble D., *Proc. Natl. Acad. Sci. USA*, 99(9): 5755-6 (2002)) myotonia (Cannon, S C, *Kidney Int.* 57(3): 772-9 (2000)), and pain (Wood, J N et al., *J. Neurobiol.*, 61(1): 55-71 (2004)). See Table I, below.

preferential expression in primary nociceptive neurons. Human genetic variants of these channels have not been associated with any inherited clinical disorder. However, aberrant expression of $Na_v1.8$ has been found in the CNS of human multiple sclerosis (MS) patients and also in a rodent model of MS (Black, J A, et al., *Proc. Natl. Acad. Sci. USA*, 97(21): 11598-602 (2000)). Evidence for involvement in nociception is both associative (preferential expression in nociceptive neurons) and direct (genetic knockout). $Na_v1.8$-null mice exhibited typical nociceptive behavior in response to acute noxious stimulation but had significant deficits in referred pain and hyperalgesia (Laird J M, et al., *J. Neurosci.*, 22(19): 8352-6 (2002)).

The TTX-sensitive subset of voltage-gated sodium channels is expressed in a broader range of tissues than the TTX-resistant channels and has been associated with a variety of human disorders. The $Na_v1.1$ channel well exemplifies this general pattern, as it is expressed in both the central and peripheral nervous system and has been associated with several seizure disorders including Generalized Epilepsy with Febrile Seizures Plus, types 1 and 2 (GEFS+1, GEFS+2), Severe Myoclonic Epilepsy of Infancy (SMEI), and others (Claes, L, et al., *Am. J. Hum. Genet.*, 68: 1327-1332 (2001); Escayg, A., *Am. J. Hum. Genet.*, 68: 866-873 (2001); Lossin, C, *Neuron*, 34: 877-884 (2002)). The $Na_v1.2$ channel is largely, if not exclusively, expressed in the central nervous system and quantitative studies indicate it is the most abundant VGSC of the CNS. Mutations of $Na_v1.2$ are also associated with seizure disorders (Berkovic, S. F., et al., *Ann. Neurol.*, 55: 550-557 (2004)) and $Na_v1.2$-null "knockout" mice exhibit perinatal lethality (Planells-Cases R et al., *Biophys. J.*,

TABLE I

| Type | Gene Symbol | Primary tissue | TTX IC-50 | Disease association | Indications |
| --- | --- | --- | --- | --- | --- |
| $Na_v1.1$ | SCN1A | CNS/PNS | 10 | Epilepsy | Pain, seizures, neurodegeneration |
| $Na_v1.2$ | SCN2A | CNS | 10 | Epilepsy | Epilepsy, neurodegeneration |
| $Na_v1.3$ | SCN3A | CNS | 15 | — | Pain |
| $Na_v1.4$ | SCN4A | Sk. muscle | 25 | Myotonia | Myotonia |
| $Na_v1.5$ | SCN5A | Heart | 2000 | Arrhythmia | Arrhythmia |
| $Na_v1.6$ | SCN8A | CNS/PNS | 6 | — | Pain, movement disorders |
| $Na_v1.7$ | SCN9A | PNS | 25 | Erythermalgia | Pain |
| $Na_v1.8$ | SCN10A | PNS | 50000 | — | Pain |
| $Na_v1.9$ | SCN11A | PNS | 1000 | — | Pain |

There are currently 9 known members of the family of voltage-gated sodium channel (VGSC) alpha subunits. Names for this family include SCNx, SCNAx, and $Na_vx.x$. The VGSC family has been phylogenetically divided into two subfamilies $Na_v1.x$ (all but SCN6A) and $Na_v2.x$ (SCN6A). The $Na_v1.x$ subfamily can be functionally subdivided into two groups, those which are sensitive to blocking by tetrodotoxin (TTX-sensitive or TTX-s) and those which are resistant to blocking by tetrodotoxin (TTX-resistant or TTX-r).

There are three members of the subgroup of TTX-resistant sodium channels. The SCN5A gene product ($Na_v1.5$, H1) is almost exclusively expressed in cardiac tissue and has been shown to underlie a variety of cardiac arrhythmias and conduction disorders (Liu H, et al., *Am. J. Pharmacogenomics*, 3(3): 173-9 (2003)). Consequently, blockers of $Na_v1.5$ have found clinical utility in treatment of such disorders (Srivatsa U, et al., *Curr. Cardiol. Rep.*, 4(5): 401-10 (2002)). The remaining TTX-resistant sodium channels, $Na_v1.8$ (SCN10A, PN3, SNS) and $Na_v1.9$ (SCN11A, NaN, SNS2) are expressed in the peripheral nervous system and show 78(6):2878-91 (2000)). Expression of the $Na_v1.4$ gene is largely restricted to skeletal muscle and, accordingly, mutations of this gene are associated with a variety of movement disorders (Ptacek, L. J., *Am. J. Hum. Genet.*, 49: 851-854 (1991); Hudson A J, Brain, 118(2): 547-63 (1995)). The majority of these disorders are related to hyperactivity or "gain-of-function" and have been found to respond to treatment with sodium channel blockers (Desaphy J F, et al., *J. Physiol.*, 554(2): 321-34 (2004)).

Neither the SCN3A nor the SCN8A VGSC genes have been conclusively linked to heritable disorders in humans. Loss-of-function mutations of the SCN8A gene are known in mice and yield increasingly debilitating phenotypes, dependent upon the remaining functionality of the gene products (Meisler M H, *Genetica*, 122(1): 37-45 (2004)). Homozygous null mutations cause progressive motor neuron failure leading to paralysis and death, while heterozygous null animals are asymptomatic. Homozygous med$^J$ mice have nearly 90% reduction in functional $Na_v1.6$ current and exhibit dystonia and muscle weakness but are still viable. Evidence for Na$_v$1.6 being important for nociception is largely associative as Na$_v$1.6 is expressed at high levels in dorsal root ganglia and can be found in spinal sensory tracts (Tzoumaka E, *J. Neurosci. Res.*, 60(1): 37-44 (2000)). It should be noted however that expression of Na$_v$1.6 is not restricted to sensory neurons of the periphery. Like the Na$_v$1.6 channel, expression of the Na$_v$1.3 VGSC can also be detected in both the central and peripheral nervous system, though levels in the adult CNS are generally much higher than PNS. During development and the early postnatal period Na$_v$1.3 is expressed in peripheral neurons but this expression wanes as the animal matures (Shah B S, *Physiol.*, 534(3): 763-76 (2001); Schaller K L, *Cerebellum*, 2(1): 2-9 (2003)). Following neuronal insult Na$_v$1.3 expression is upregulated, more closely mimicking the developmental expression patterns (Hains B C, *J. Neurosci.*, 23(26): 8881-92 (2003)). Coincident with the recurrence of Na$_v$1.3 expression is the emergence of a rapidly re-priming sodium current in the injured axons with a biophysical profile similar to Na$_v$1.3 (Leffler A, et al., *J. Neurophysiol.*, 88(2): 650-8 (2002)). Treatment of injured axons with high levels of GDNF has been shown to diminish the rapidly repricing sodium current and reverses thermal and mechanical pain-related behaviors in a rat model of nerve injury, presumably by down-regulating the expression of Na$_v$1.3 (Boucher T J, *Curr. Opin. Pharmacol.*, 1(1): 66-72 (2001)). Specific down-regulation of Na$_v$1.3 via treatment with antisense oligonucleotides has also been shown to reverse pain-related behaviors following spinal cord injury (Haim B C, *J. Neurosci.*, 23(26): 8881-92 (2003)).

The Na$_v$1.7 (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows ~90% amino acid identity between the human and rat genes (Toledo-Aral et al., *Proc. Natl. Acad. Sci. USA*, 94(4): 1527-1532 (1997)).

An increasing body of evidence suggests that Na$_v$1.7 may play a key role in various pain states, including acute, inflammatory and/or neuropathic pain. Deletion of the SCN9A gene in nociceptive neurons of mice led to a reduction in mechanical and thermal pain thresholds and reduction or abolition of inflammatory pain responses (Nassar et al., *Proc Natl Acad Sci USA*, 101(34): 12706-11 (2004)). In humans, Na$_v$1.7 protein has been shown to accumulate in neuromas, particularly painful neuromas (Kretschmer et al., *Acta. Neurochir. (Wien)*, 144(8): 803-10 (2002)). Mutations of Na$_v$1.7, both familial and sporadic, have also been linked to primary erythermalgia, a disease characterized by burning pain and inflammation of the extremities (Yang et al., *J. Med. Genet.*, 41(3): 171-4 (2004)). Congruent with this observation is the report that the non-selective sodium channel blockers lidocaine and mexiletine can provide symptomatic relief in cases of familial erythermalgia (Legroux-Crepel et al., *Ann. Dermatol Venereol.*, 130: 429-433).

Sodium channel-blocking agents have been reported to be effective in the treatment of various disease states, and have found particular use as local anesthetics and in the treatment of cardiac arrhythmias. It has also been reported that sodium channel-blocking agents may be useful in the treatment of pain, including acute, chronic, inflammatory and/or neuropathic pain; see, for example, Wood, J N et al., *J. Neurobiol.*, 61(1): 55-71 (2004). Preclinical evidence demonstrates that sodium channel-blocking agents can suppress neuronal firing in peripheral and central sensory neurons, and it is via this mechanism that they may be useful for relieving pain. In some instances abnormal or ectopic firing can originate from injured or otherwise sensitized neurons. For example, it has been shown that sodium channels can accumulate in peripheral nerves at sites of axonal injury and may function as generators of ectopic firing (Devor et al. *J. Neurosci.*, 132: 1976 (1993)). Changes in sodium channel expression and excitability have also been shown in animal models of inflammatory pain where treatment with proinflammatory materials (CFA, Carrageenan) promoted pain-related behaviors and correlated with increased expression of sodium channel subunits (Gould et al., *Brain Res.*, 824(2): 296-9 (1999); Black et al., *Pain*, 108(3): 237-47 (2004)). Alterations in either the level of expression or distribution of sodium channels, therefore, may have a major influence on neuronal excitability and pain-related behaviors.

Many patients with either acute or chronic pain disorders respond poorly to current pain therapies and resistance or insensitivity to opiates is common. In addition, many of the currently available treatments have undesirable side effects. It has been reported that there is no treatment to prevent the development of neuropathic pain or to control established neuropathic pain. Mannion et al., *Lancet*, 353: 1959-1964 (1999).

Ohkawa et al. have described a class of cyclic ethers that are of use as sodium channel blockers (U.S. Pat. No. 6,172,085).

In view of the limited number of agents presently available and the low levels of efficacy of the available agents, there is a pressing need for compounds that are potent, specific inhibitors of ion channels implicated in neuropathic pain. The present invention provides such compounds, methods of using them, and compositions that include the compounds.

SUMMARY OF THE INVENTION

It has now been discovered that various substituted aryl sulfonamides are potent modulators of sodium channels. In the discussion that follows, the invention is exemplified by reference to the inhibition of sodium channels that are localized in the peripheral nervous system, and in particular those compounds that are selective inhibitors of TTX-s sodium channels, and are useful for treating pain through the inhibition of sodium ion flux through channels that include a TTX-s sodium channel subunit. The compounds, compositions and methods of the present invention are useful for treating diseases in which modulating one or more TTX-s sodium channels provides relief from the disease. Of particular interest is the use of the compounds, compositions and methods of the invention for treating pain and central or peripheral nervous system disorders, preferably peripheral nervous system disorders. The present invention is of use for treating acute, chronic, inflammatory, and/or neuropathic pain.

The present invention provides compounds that are useful in the treatment of diseases through the modulation of sodium ion flux through voltage-dependent sodium channels. More particularly, the invention provides compounds, compositions and methods that are useful in ameliorating or alleviating conditions susceptible to such ion channel modulation as more fully described below.

In one aspect, the invention provides a compound according to Formula I:

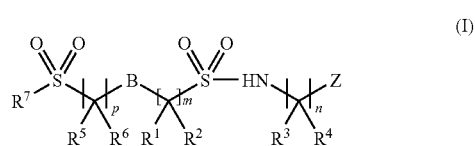

wherein $R^1$, $R^2$, $R^3$, $R^4$, $R^5$ and $R^6$ are members independently selected from H, halogen, $CF_3$, substituted or unsubstituted alkyl, substituted or unsubstituted heteroalkyl, substituted or unsubstituted aryl, substituted or unsubstituted heteroaryl, and substituted or unsubstituted heterocycloalkyl, wherein two or more members selected from $R^1$, $R^2$, $R^3$, $R^4$, $R^5$ and $R^6$ are optionally joined to form a 4-8-member substituted or unsubstituted ring system, optionally including 1-3 heteroatoms; $R^7$ is a member selected from substituted or unsubstituted alkyl, substituted or unsubstituted heteroalkyl, substituted or unsubstituted heterocycloalkyl, substituted or unsubstituted aryl and substituted or unsubstituted heteroaryl, with the proviso that $R^7$ is other than methyl, and $R^7$ is not bound to the $S(O)_2$ moiety of Formula I through a sulfur-nitrogen bond; B is a member selected from substituted or unsubstituted cycloalkyl, substituted or unsubstituted aryl and substituted or unsubstituted heteroaryl; wherein B is optionally joined to $R^7$ to form a fused ring system; Z is a substituted or unsubstituted five-member heteroaryl moiety; and m, n and p are members independently selected from the integers from 0 to 5. In some embodiments, if m is 0, p is 0 and n is not zero, then $R^7$ is substituted or unsubstituted alkyl, substituted or unsubstituted heteroalkyl, substituted or unsubstituted heterocycloalkyl.

In one embodiment, the present invention provides the compounds having Formula (I) or a pharmaceutically acceptable salt or solvate thereof, wherein $R^1$, $R^2$, $R^3$, $R^4$, $R^5$ and $R^6$ are each independently selected from H, halogen, $C_{1-8}$haloalkyl, $C_{1-8}$alkyl, aryl, heteroaryl or heterocycloalkyl, wherein two or more members selected from $R^1$, $R^2$, $R^3$, $R^4$, $R^5$ and $R^6$ are optionally joined to form a 4-8-membered carbocyclic or heterocyclic ring having from 1-3 heteroatoms as ring members selected from O, N or S. In certain instances, two members of $R^1$, $R^2$, $R^3$, $R^4$, $R^5$ and $R^6$ are attached to the same carbon atom and are combined with the carbon atom to which they are attached to form a 4-8 membered carbocyclic or heterocyclic ring having from 1-3 heteroatoms as ring members selected from O, N or S.

$R^7$ is a member selected from $C_{1-8}$alkyl, heterocycloalkyl, aryl and heteroaryl, with the proviso that $R^7$ is other than methyl, and $R^7$ is not bound to the $S(O)_2$ moiety of Formula (I) through the sulfur-nitrogen bond; wherein the aliphatic portion of $R^1$, $R^2$, $R^3$, $R^4$, $R^5$, $R^6$, $R^7$ groups is optionally independently substituted with from 1-3 $R^a$ substituents selected from the group consisting of —$OR^b$, =O, =$NR^b$, =N—$OR^b$, —$NR^bR^b$, —$SR^b$, -halogen, —$Si(R^b)_3$, —OC(O)$R^b$, —C(O)$R^b$, —$CO_2R^b$, —CON($R^b$)$_2$, —OC(O)N($R^b$)$_2$, —$NR^b$C(O)$R^b$, —$NR^b$—C(O)N($R^b$)$_2$, —$NR^b$C(O)$_2R^b$, —$NR^h$—C($NR^bR^b$)=$NR^b$, —S(O)$R^b$, —S(O)$_2R^b$, —S(O)$_2$N($R^b$)$_2$, —$NRSO_2R^b$, $C_{1-8}$alkyl, —CN, —$R^b$ and —$NO_2$, wherein each $R^b$ is independently H, $C_{1-8}$alkyl, aryl or heteroaryl and two $R^b$ groups when attached to the same nitrogen atom are optionally combined together with the nitrogen atom to which they are attached to form a 5-6 membered ring having from 0-2 additional heteroatoms as ring members selected from O, N or S; wherein each $R^b$ group is further optionally independently substituted with from 1-3 $R^c$ substituents selected from —$OR^d$, =O, =$NR^d$, =N—$OR^d$, —$NR^dR^d$, —$SR^d$, -halogen, —$Si(R^d)_3$, —OC(O)$R^d$, —(O)$R^d$, $CO_2R^d$, —CON($R^d$)$_2$, —OC(O)N($R^d$)$_2$, —$NR^d$C(O)$R^d$, —$NR^d$—C(O)N($R^d$)$_2$, —$NR^d$C(O)$_2R^d$, —$NR^d$—C($NR^dR^d$)=$NR^d$, —S(O)$R^d$, —S(O)$_2R^d$, —S(O)$_2$N($R^d$)$_2$, —$NRSO_2R^d$, $C_{1-8}$alkyl, —CN and —$NO_2$, wherein $R^d$ is —H, $C_{1-8}$alkyl or aryl and two $R^d$ groups when attached to the same nitrogen atom are optionally combined together with the nitrogen atom to which they are attached to form a 5-6 membered ring having from 0-2 additional heteroatoms as ring members selected from O, N or S; the aryl or heteroaryl moiety of $R^1$, $R^2$, $R^3$, $R^4$, $R^5$, $R^6$ and $R^7$ groups are each optionally independently substituted with from 1-3 $R^e$ substituents independently selected from halogen, —$OR^f$, —$NR^fR^f$, —$SR^f$, -halogen, —$Si(R^f)_3$, —OC(O)$R^f$, —C(O)$R^f$, —$CO_2R^f$, —CON($R^f$)$_2$, —OC(O)N($R^f$)$_2$, —$NR^f$C(O)$R^f$, —$NR^f$—C(O)N($R^f$)$_2$, —$NR^f$C(O)$_2R^f$, —$NR^f$—C($NR^fR^f$)=$NR^f$, —S(O)$R^f$, —S(O)$_2R^f$, —S(O)$_2NR^fR^f$, —$NRSO_2R^f$, $C_{1-8}$alkyl, —CN and —$NO_2$, $C_{1-8}$alkyl, —$N_3$, —CH(Ph)$_2$, fluoro$C_{1-4}$alkoxy, and fluoro$C_{1-4}$alkyl, wherein $R^f$ is —H, $C_{1-8}$alkyl, aryl or heteroaryl and two $R^f$ groups when attached to the same nitrogen atom are optionally combined together with the nitrogen atom to which they are attached to form a 5-6 membered ring having from 0-2 additional heteroatoms as ring members selected from O, N or S; wherein the aliphatic portion of $R^f$ group is further optionally independently substituted with from 1-3 $R^a$ substituents and the aromatic portion of the $R^f$ group is further optionally independently substituted with from 1-3 $R^g$ substituents independently selected from —$OR^h$, —$NR^hR^h$, —$SR^h$, —halogen, —$Si(R^h)_3$, —OC(O)$R^h$, —C(O)$R^h$, —$CO_2R^h$, —CON($R^h$)$_2$, —OC(O)N($R^h$)$_2$, —$NR^h$C(O)$R^h$, —$NR^h$—C(O)N($R''$)$_2$, —$NR^h$C(O)$_2R^h$, —$NR^h$—C($NR^hR^h$)=$NR^h$, —S(O)$R^h$, —S(O)$_2R^h$, —S(O)$_2NR^hR^h$, —$NRSO_2R^h$, —CN and —$NO_2$, $C_{1-8}$ alkyl, —$N_3$, —CH(Ph)$_2$, fluoro$C_{1-4}$alkoxy, and fluoro $C_{1-4}$alkyl, wherein $R^h$ is —H or $C_{1-8}$alkyl; wherein the two $R^h$ groups when attached to the same nitrogen atom are optionally combined with the nitrogen atom to which they are attached to form a 5-6-membered ring having from 0-2 additional heteroatoms as ring members selected from O, N or S; B is a member selected from $C_{3-7}$cycloalkylene, arylene and heteroarylene, or B is optionally joined to $R^7$ to form a fused ring, wherein the cycloalkylene is optionally independently substituted with from 1-3 $R^h$ substituents and the arylene or heteroarylene moiety is optionally independently substituted with from 1-3 $R^g$ substituents;

Z is a five-membered heteroaryl having from 1-4 heteroatoms as ring members selected from O, N or S, wherein Z is optionally substituted with from 1-3 $R^e$ substituents;

the subscripts m, n and p are each independently selected from the integers from 0 to 5;

with the proviso when p and m are 0, n is not 0, and $R^7$ is other than aryl or heteroaryl.

In some embodiments of the above, at each occurrence of each of the recitals in the description, the term "alkyl" by itself or as part of another substituent, means an unsubstituted, fully saturated, straight or branched chain hydrocarbon radical; the term "cycloalkyl" by itself or as part of another substituent means an unsubstituted, fully saturated, cyclic hydrocarbon radical; and the term "aryl" by itself or as part or another substituent means a monovalent monocyclic, bicyclic or polycyclic polyunsaturated aromatic hydrocarbon radical.

The compounds of the invention include salts (e.g., pharmaceutically acceptable salts), solvates or hydrates and prodrugs of the species according to Formula I, IA, Ia, Ib and Ic. The compounds of the invention are preferably substantially free of impurities.

In another aspect, the present invention provides pharmaceutical compositions comprising a pharmaceutically acceptable excipient and a compound as provided herein (e.g., compounds of any of Formulas I, IA, Ia, Ib and Ic).

In yet another aspect, the present invention provides a method for modulating the activity of a sodium channel in a subject, comprising administering to a subject an amount of a compound as provided herein (e.g., compounds of any of Formulas I, IA, Ia, Ib and Ic), which is sufficient to modulate the activity.

In still another aspect, the present invention provides a method of ameliorating or alleviating a condition in a subject. The condition can be a member selected from, among others, pain, irritable bowel syndrome, Crohn's disease, epilepsy, seizures multiple sclerosis, bipolar depression and tachyarrhythmias. The method comprises administering to the subject an amount of a compound (e.g., compounds of any of Formulas I, IA, Ia, Ib and Ic) of the invention as described herein sufficient to ameliorate or alleviate said condition.

Additional aspects, advantages and objects of the present invention will be apparent from the detailed description that follows.

DETAILED DESCRIPTION OF THE INVENTION

Abbreviations

The abbreviations used herein generally have their conventional meaning within the chemical and biological arts. For example: CHO, Chinese hamster ovary; EBSS, Earl's Balanced Salt Solution; SDS, sodium dodecyl sulfate; $Et_3N$, triethylamine; MeOH, methanol; and DMSO, dimethylsulfoxide.

DEFINITIONS

The term "pain" refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic neuropathy (see, e.g., Harrison's Principles of Internal Medicine, pp. 93-98 (Wilson et al., eds., 12th ed. 1991); Williams et al., *J. of Med. Chem.* 42: 1481-1485 (1999), herein each incorporated by reference in their entirety).

"Somatic" pain, as described above, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

"Neuropathic" pain, as described above, refers to pain resulting from injury to or chronic changes in peripheral and/or central sensory pathways, where the pain often occurs or persists without an obvious noxious input.

"Acute pain", as described above, refers to pain which is marked by short duration or a sudden onset.

"Chronic pain", as described above, refers to pain which is marked by long duration or frequent recurrence.

"Inflammatory pain", as described above, refers to pain which is produced as a symptom or a result of inflammation or an immune system disorder.

"Visceral pain", as described above, refers to pain which is located in an internal organ.

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Compound of the invention," as used herein refers to the compounds discussed herein, pharmaceutically acceptable salts, solvates and prodrugs of these compounds.

"Inhibiting" and "blocking," are used interchangeably herein to refer to the partial or full blockade of a voltage sodium gated channel by a compound of the invention, which leads to a decrease in ion flux either into or out of a cell in which a voltage-gated sodium channel is found.

Where substituent groups are specified by their conventional chemical formulae, written from left to right, they equally encompass the chemically identical substituents, which would result from writing the structure from right to left, e.g., —$CH_2O$— is preferably intended to also recite —$OCH_2$—.

The term "alkyl," by itself or as part of another substituent, means, unless otherwise stated, a straight- or branched-chain, or cyclic hydrocarbon radical, or combination thereof, which may be fully saturated, mono- or polyunsaturated and can include mono-, di- and multivalent radicals, having the number of carbon atoms designated (i.e. $C_{1-10}$ or $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, also preferably include those derivatives of alkyl defined in more detail below, such as "heteroalkyl." Alkyl groups that are limited to hydrocarbon groups are termed "homoalkyl". The term "alkyl", as used herein refers to alkyl, alkenyl and alkynyl moieties, each of which can be mono-, di- or polyvalent species. Alkyl groups are preferably substituted, e.g., with one or more group referred to herein below as an "alkyl group substituent." In one embodiment, alkyl includes a straight or branched chain fully saturated aliphatic hydrocarbon radicals having the number of carbon atoms designated. For example, $C_{1-8}$alkyl refers to a hydrocarbon radical straight or branched having 1, 2, 3, 4, 5, 6, 7 or 8 carbon atoms and includes, but are not limited to, $C_{1-2}$alkyl, $C_{1-4}$alkyl, $C_{2-6}$alkyl, $C_{2-4}$alkyl, $C_{1-6}$alkyl, $C_{2-8}$alkyl, $C_{1-7}$alkyl, $C_{2-7}$alkyl and $C_{3-8}$alkyl.

The term "alkylene" by itself or as part of another substituent means a divalent radical derived from an alkane having the number of carbon atoms indicated in the prefix, as exemplified, but not limited, by —$CH_2CH_2CH_2CH_2$—, and further includes those groups described below as "heteroalkylene." For example, ($C_1$-$C_6$)alkylene is meant to include methylene, ethylene, propylene, 2-methylpropylene, pentylene, and the like. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight- or branched-chain, or cyclic alkyl radical consisting of the stated number of carbon atoms and at least one heteroatom selected from the group consisting of B, O, N, Si and S, wherein the heteroatom may optionally be oxidized and the nitrogen atom may optionally be quaternized. The heteroatom(s) may be placed at any internal position of the heteroalkyl group or at a terminus of the chain, e.g., the position through which the alkyl group is attached to the remainder of the molecule. Examples of "heteroalkyl" groups include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Two or more heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent refers to a substituted or unsubstituted divalent heteroalkyl radical, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents —C(O)$_2$R'— and, preferably, —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Preferably, "cycloalkyl" refers to hydrocarbon rings having the indicated number of ring atoms (e.g., $C_{3-6}$ cycloalkyl) and being fully saturated or having no more than one double bond between ring vertices. One or two C atoms may optionally be replaced by a carbonyl. "Cycloalkyl" is also meant to refer to bicyclic and polycyclic hydrocarbon rings such as, for example, bicyclo[2.2.1]heptane, bicyclo[2.2.2]octane, etc. The term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized, the remaining ring atoms being C, where one or two C atoms may optionally be replaced by a carbonyl. The heterocycloalkyl may be a monocyclic, a bicyclic or a polycylic ring system of 3 to 12, preferably 5 to 8, ring atoms in which one to five ring atoms are heteroatoms. The heterocycloalkyl can also be a heterocyclic alkyl ring fused with an aryl or a heteroaryl ring. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, pyrrolidinyl, piperidinyl, imidazolidinyl, pyrazolidinyl, butyrolactam radical, valerolactam radical, imidazolidinone radical, hydantoin, dioxolane radical, phthalimide radical, piperidine, 1,4-dioxane radical, morpholinyl, thiomorpholinyl, thiomorpholinyl-S-oxide, thiomorpholinyl-S,S-oxide, piperazinyl, pyranyl, pyridine radical, 3-pyrrolinyl, thiopyranyl, pyrone radical, tetrahydrofuranyl, tetrahydrothiophenyl, quinuclidinyl, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "cycloalkylene" refers to a divalent cyclic carbocycle radical, preferably from cycloalkane radical containing from 4 to 8, preferably 5 or 6, carbon atoms and one or more double bonds. Exemplary cycloalkylene groups include, but are not limited to, cyclopentylene, cyclohexylene, cyclopentadienylene and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings, one or more of which is optionally a cycloalkyl or heterocycloalkyl), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of "aryl group substituents" described below.

The term "arylene" by itself or as part of another substituent means a divalent hydrocarbon radical derived from aryl, as exemplified by phenylene, biphenylene, and the like.

The term "heteroarylene" by itself or as part of another substituent means a divalent radical derived from heteroaryl, for example, 5- or 6-membered heteroaryl, as exemplified by pyridinylene, imidazolylene, thiophenylene, and the like. Representative heteroarylene includes 2,5-pyridinylene, 3,6-pyridinylene, 2,6-pyrazinylene, 2,5-pyrazinylene, 2,4-primidinylene, 2,3-primidinylene, 2,5-primidinylene3,5-primidinylene, 3,6-pyridazinylene, or a divalent radical derived from 1-pyrrolyl, 2-pyrrolyl, 3-pyrrolylene, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl and Z is 2-thiazolyl, 4-thiazolyl, and 5-thiazolyl and the like.

For brevity, the term "aryl" when used in combination with other terms (e.g., aryloxy, arylthioxy, arylalkyl) preferably includes both homoaryl and heteroaryl rings as defined above. Thus, the term "arylalkyl" optionally includes those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R") =NR"", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" includes groups with carbon atoms bound to groups other than hydrogen, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C (NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

As used herein, the term "heteroatom" includes oxygen (O), nitrogen (N), sulfur (S) and silicon (Si).

"Tautomer" refers to alternate forms of a molecule that differ in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. Where the compound contains, for example, a keto or oxime group or an aromatic moiety, tautomeric isomerism ('tautomerism') can occur. It follows that a single compound may exhibit more than one type of isomerism. A person of ordinary skill in the art would recognize that other tautomeric ring atom arrangements are possible.

The term "salt(s)" includes salts of the compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts.

When the compound prepared by a method of the invention is a pharmacological agent, the salt is preferably a pharmaceutically acceptable salt. Examples of pharmaceutically acceptable salts are presented hereinabove, and are generally known in the art. See, for example, Wermuth, C., PHARMACEUTICAL SALTS: PROPERTIES, SELECTION AND USE-A HANDBOOK, Verlag Helvetica Chimica Acta (2002)

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds that are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

As used herein, and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise NO, $NO_2$, —ONO, or —$ONO_2$ moieties. The term "prodrug" is accorded a meaning herein such that prodrugs do not encompass the parent compound of the prodrug. When used to describe a compound of the invention, the term "prodrug" may also to be interpreted to exclude other compounds of the invention.

As used herein, and unless otherwise indicated, the terms "biohydrolyzable carbamate," "biohydrolyzable carbonate," "biohydrolyzable ureide" and "biohydrolyzable phosphate" mean a carbamate, carbonate, ureide and phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, and unless otherwise indicated, the term "biohydrolyzable ester" means an ester of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters.

As used herein, and unless otherwise indicated, the term "biohydrolyzable amide" means an amide of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable amides include, but are not limited to, lower alkyl amides, .alpha.-amino acid amides, alkoxyacyl amides, and alkylaminoalkylcarbonyl amides.

Certain compounds of the present invention can exist in unsolvated forms as well as solvated forms, including hydrated forms. "Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylfonnamide, tetrahydrofuran, dimethylsulfoxide, and water. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention. These isomers can be resolved or asymmetrically synthesized using conventional methods to render the isomers "optically pure", i.e., substantially free of its other isomers. If, for instance, a particular enantiomer of a compound of the present invention is desired, it may be prepared by asymmetric synthesis, or by derivation with a chrial auxilliary, where the resulting diastereomeric mixture is separated and the auxilliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diasteromers thus formed by fractional crystallization or chromatagraphic means well known in the art, and subsequent recovery of the pure enantiomers.

As used herein, and unless otherwise indicated, a composition that is "substantially free" of a compound means that the composition contains less than about 20% by weight, more preferably less than about 10% by weight, even more preferably less than about 5% by weight, and most preferably less than about 3% by weight of the compound.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

DESCRIPTION OF THE EMBODIMENTS

I. The Compounds

In one aspect, the present invention provides a compound according to Formula I:

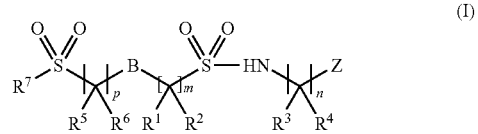

(I)

wherein
$R^1$, $R^2$, $R^3$, $R^4$, $R^5$ and $R^6$ are members independently selected from H, halogen, $CF_3$, substituted or unsubstituted alkyl, substituted or unsubstituted heteroalkyl, substituted or unsubstituted aryl, substituted or unsubstituted heteroaryl, and substituted or unsubstituted heterocycloalkyl, wherein two or more members selected from $R^1$, $R^2$, $R^3$, $R^4$, $R^5$ and $R^6$ are optionally joined to form a 4-8-member substituted or unsubstituted ring system, optionally including 1-3 heteroatoms; $R^7$ is a member selected from substituted or unsubstituted alkyl, substituted or unsubstituted heteroalkyl, substituted or unsubstituted heterocycloalkyl, substituted or unsubstituted aryl and substituted or unsubstituted heteroaryl, with the proviso that $R^7$ is other than methyl, and $R^7$ is not bound to the $S(O)_2$ moiety of Formula I through a sulfur-nitrogen bond; B is a member selected from substituted or unsubstituted cycloalkyl, substituted or unsubstituted aryl and substituted or unsubstituted heteroaryl, wherein B is optionally joined to $R^7$ to form a fused ring system; Z is a substituted or unsubstituted five-member heteroaryl moiety; and m, n and p are members independently selected from the integers from 0 to 5. In some embodiments, p and m are independently an integer from 1-5. In other embodiments, p and m are both zero, n is an integer of 1-5 and $R^7$ is a member selected from substituted or unsubstituted alkyl, substituted or unsubstituted heteroalkyl and substituted or unsubstituted heterocycloalkyl.

In one embodiment, m and p are not both zero, and m and p are each independently selected from 0, 1, 2, 3, 4 and 5. In another embodiment, in and p are both zero. In yet another embodiment, m, p and n are zero. In still another embodiment, in and p are zero and n is an integer of 1, 2, 3, 4, or 5. In another embodiment, p is 0. In yet another embodiment, n is 0. In still another embodiment, m is 0. In one embodiment, p is 0, m and n are each independently selected from 0, 1, 2, 3, 4, or 5. In another embodiment, in is 0, p and n are each independently selected from 0, 1, 2, 3, 4, or 5. In yet another embodiment, n is 0, p and m are each independently selected from 0, 1, 2, 3, 4, or 5

In some embodiments, the present invention provides compounds having Formula (IA):

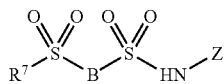

IA or pharmaceutically acceptable salts or solvates thereof.

In Formula (IA), $R^7$ is a member selected from $C_{1-8}$alkyl, heterocycloalkyl, aryl and heteroaryl, with the proviso that $R^7$ is other than methyl, and $R^7$ is not bound to the $S(O)_2$ moiety of Formula (IA) through a sulfur-nitrogen bond. The aliphatic portion of $R^7$ group is optionally substituted with from 1-3 $R^a$ substituents independently selected from the group consisting of —$OR^b$, =O, =$NR^b$, =N—$OR^b$, —$NR^bR^b$, —$SR^b$, -halogen, —Si$(R^b)_3$, —OC(O)$R^b$, —C(O)$R^b$, —CO$_2R^b$, —CON$(R^b)_2$, —OC(O)N$(R^b)_2$, —$NR^b$C(O)$R^b$, —$NR^b$—C(O)N$(R^b)_2$, —$NR^b$C(O)$_2R^b$, $NR^b$—C(N$R^bR^b$)=$NR^b$, —S(O)$R^b$, —S(O)$_2R^b$, —S(O)$_2$N$(R^b)_2$, —NRSO$_2R^b$, $C_{1-8}$alkyl, —CN, —$R^b$ and —NO$_2$, wherein each $R^b$ is independently H, $C_{1-8}$alkyl, aryl or heteroaryl and two $R^b$ groups when attached to the same nitrogen atom are optionally combined together with the nitrogen atom to which they are attached to form a 5-6 membered ring having from 0-2 additional heteroatoms as ring members selected from O, N or S; wherein $R^b$ group is further optionally substituted with from 1-3 $R^c$ substituents independently selected from —$OR^d$, =O, =$NR^d$, =N—$OR^d$, —$NR^dR^d$, —$SR^d$, -halogen, —Si$(R^d)_3$, —OC(O)$R^d$, —C(O)$R^d$, —CO$_2R^d$, —CON$(R^d)_2$, OC(O)N$(R^d)_2$, —$NR^d$C(O)$R^d$, —$NR^d$—C(O)N$(R^d)_2$, —$NR^d$C(O)$_2R^d$, —$NR^d$—C(N$R^dR^d$)=$NR^d$, —S(O)$R^d$, —S(O)$_2R^d$, —S(O)$_2$N$(R^d)_2$, —NRSO$_2R^d$, $C_{1-8}$alkyl, —CN and —NO$_2$, wherein $R^d$ is —H, $C_{1-8}$alkyl or aryl and two $R^d$ groups when attached to the same nitrogen atom are optionally combined together with the nitrogen atom to which they are attached to form a 5-6 membered ring having from 0-2 additional heteroatoms as ring members selected from O, N or S; the aryl or heteroaryl moiety of $R^7$ group is optionally substituted with from 1-3 $R^e$ substituents independently selected from halogen, —$OR^f$, —$NR^fR^f$, —$SR^f$, -halogen, —Si$(R^f)_3$, —OC(O)$R^f$, —C(O)$R^f$, —CO$_2R^f$, —CON$(R^f)_2$, —OC(O)N$(R^f)_2$, —$NR^f$C(O)$R^f$, —$NR^f$—C(O)N$(R^f)_2$, —$NR^f$C(O)$_2R^f$, —$NR^f$—C(N$R^fR^f$)=$NR^f$, —S(O)$R^f$, —S(O)$_2R^f$, —S(O)$_2$N$R^fR^f$, —NRSO$_2R^f$, $C_{1-8}$alkyl, —CN and —NO$_2$, $C_{1-8}$alkyl, —N$_3$, —CH(Ph)$_2$, fluoro$C_{1-4}$alkoxy, and fluoro$C_{1-4}$alkyl, wherein $R^f$ is —H, $C_{1-8}$alkyl, aryl or heteroaryl and two $R^f$ groups when attached to the same nitrogen atom are optionally combined together with the nitrogen atom to which they are attached to form a 5-6 membered ring having from 0-2 additional heteroatoms as ring members selected from O, N or S; wherein the aliphatic portion of $R^f$ group is further optionally independently substituted with from 1-3 $R^a$ substituents and the aromatic portion of the $R^f$ group is further optionally independently substituted with from 1-3 $R^g$ substituents selected from —$OR^h$, —$NR^hR^h$, —$SR^h$, —halogen, —Si$(R^h)_3$, —OC(O)$R^h$, —C(O)$R^h$, —CO$_2R^h$, —CON$(R^h)_2$, —OC(O)N$(R^h)_2$, —$NR^h$C(O)$R^h$, —$NR^h$—C(O)N$(R^h)_2$, —$NR^h$C(O)$_2R^h$, —$NR^h$—C(N$R^hR^h$)=$NR^h$, —S(O)$R^h$, —S(O)$_2R^h$, —S(O)$_2$N$R^hR^h$, —NRSO$_2R^h$, —CN and —NO$_2$, $C_{1-8}$alkyl, —N$_3$, —CH(Ph)$_2$, fluoro$C_{1-4}$alkoxy, and fluoro$C_{1-4}$alkyl, wherein $R^h$ is —H or $C_{1-8}$alkyl; wherein the two $R^h$ groups when attached to the same nitrogen atom are optionally combined with the nitrogen atom to which they are attached to form a 5-6-membered ring having from 0-2 additional heteroatoms as ring members selected from O, N or S. B is a member selected from $C_{3-7}$cycloalkylene, arylene and heteroarylene, or B is optionally joined to $R^7$ to form a fused ring, wherein the cycloalkylene is optionally independently substituted with from 1-3 $R^b$ substituents and the arylene or heteroarylene moiety is optionally independently substituted with from 1-3 $R^g$ substituents. Z is a five-membered heteroaryl having from 1-4 heteroatoms as ring members selected from O, N or S, wherein Z is optionally substituted with from 1-3 $R^e$ substituents.

In some embodiments, with respect to the recitals for Formula I and/or IA, at each recital of each of the terms, the term "alkyl" by itself or as part of another substituent, means an unsubstituted, fully saturated, straight or branched chain hydrocarbon radical; the term "cycloalkyl" by itself or as part of another substituent means an unsubstituted, fully saturated, cyclic hydrocarbon radical; and the term "aryl" by itself or as part or another substituent means a monovalent monocyclic, bicyclic or polycyclic polyunsaturated aromatic hydrocarbon radical.

In one group of embodiments of the compounds having Formula (I), or pharmaceutically acceptable salts or solvates thereof, $R^1$, $R^2$, $R^3$, $R^4$, $R^5$ and $R^6$ are each independently selected from H, halogen, $C_{1-8}$haloalkyl, $C_{1-8}$alkyl, aryl, heteroaryl or heterocycloalkyl, wherein two or more members selected from $R^1$, $R^2$, $R^3$, $R^4$, $R^5$ and $R^6$ are optionally joined to form a 4-8-member carbocyclic or heterocyclic ring having from 1-3 heteroatoms as ring members selected from O, N or S. In certain instances, $R^1$, $R^2$, $R^3$, $R^4$, $R^5$ and $R^6$ are each independently —H or $C_{1-8}$alkyl. In other instances, $R^1$, $R^2$, $R^3$, $R^4$, $R^5$ and $R^6$ are —H or $C_{1-8}$alkyl.

In one group of embodiments of the compounds having Formula (I) or (IA), or pharmaceutically acceptable salts or solvates thereof, B is an arylene or a 6-membered heteroarylene having from 1-3 nitrogen heteroatoms as ring members, each of which is optionally substituted with 1-2 substituents selected from the group consisting of halogen, —$OR^h$, $C_{1-8}$alkyl, $C_{1-8}$haloalkyl, $C_{1-8}$haloalkoxy and —CN. In certain instances, B is an arylene, optionally substituted with from 1-2 members selected from halogen, —OH, $C_{1-8}$alkyl, —CN, CF$_3$ or —OCF$_3$. In other instances, B is phenylene, optionally substituted with 1-2 members selected from halogen, —OH, $C_{1-8}$alkyl, —CN, CF$_3$ or —OCF$_3$. In yet other instances, B is phenylene. In some occurrences, B is 2-fluorophenylene, 4-fluorophenylene, 2,4-difluorophenylene, 2,5-difluorophenylene, 2,6-difluorophenylene, 3,5-difluorophenylene, 3,6-difluorophenylene, 2-chlorophenylene, 4-chlorophenylene, 2,4-chlorophenylene, 2-trifluorohenylene, 4-trifluorophenylene, 2,4-bis(trifluoro)phenylene or 2,6-bis(trifluoro)phenylene.

In one group of embodiments of the compounds having Formula (I) or (IA), or pharmaceutically acceptable salts or solvates thereof, $R^7$ is aryl, aryl-$C_{1-8}$alkyl or heteroaryl-$C_{1-8}$alkyl, wherein the aryl or heteroaryl moiety is optionally substituted with from 1-3 $R^e$ substituents. In one group of instances, $R^7$ is aryl or aryl-$C_{1-8}$alkyl, optionally the aryl moiety is substituted with from 1-3 $R^e$ substituents. In a second group of instances, $R^7$ is aryl or aryl-$C_{1-8}$alkyl, optionally the aryl moiety is substituted with from 1-3 members selected from the group consisting of halogen, $C_{1-8}$alkyl, $C_{1-8}$haloalkyl, $C_{1-8}$haloalkoxy, —CN and —$NO_2$. In a third group of instances, $R^7$ is aryl or aryl-$C_{1-8}$alkyl, optionally the aryl moiety is independently substituted with from 1-3 members selected from the group consisting of —F, —Cl, —$CF_3$ and $CF_3O$—. In a fourth group of instances, $R^7$ is phenyl or phenyl-$C_{1-8}$alkyl, optionally the phenyl moiety is substituted with from 1-3 members selected from the group consisting of —F, —Cl, —$CF_3$ and $CF_3O$—. In a fifth group of instances, $R^7$ is aryl-$(CH_2)_q$— or heteroaryl-$(CH_2)_q$—, wherein the aryl or heteroaryl moiety is optionally substituted with from 1-3 $R^e$ substituents and the subscript q is each independently an integer of from 1-8. In some occurrences of the fifth instances, aryl is phenyl and q is 1, 2, 3, 4, 5 or 6. In other occurrences of the fifth instances, heteroaryl is a 5- or 6-membered heteroaryl.

In one group of embodiments of the compounds having Formula (I) or (IA), or pharmaceutically acceptable salts or solvates thereof, Z is thiazolyl, 2-thiazolyl, 3-pyrazolyl, 4-pyrazolyl, 5-pyrazolyl, isoxazolyl, imidazolyl, 1,2,4-triazolyl, 1,2,3-thiadiazolyl, 1,3,4-thiadiazolyl, 1,3,4-oxadiazolyl, 1,2,5-thiadiazol-4yl, 1,2,5-oxadiazol-4yl, 1,2,3,5-thiatriazol-4yl, 1,2,3,4-thiatriazol-5yl, 1,2,3,5-oxatriazol-yl, 1,2,3,4-oxatriazol-5yl, benzimidazolyl, benzoxazolyl, benzthiazolyl, tetrahydrobenzothiazolyl or dihydrobenzothiazolone, each of which is optionally substituted with 1-2 members selected from the group consisting of $C_{1-8}$haloalkyl, —CN, halogen, $C_{3-7}$cycloalkyl, aryl, $C_{1-8}$alkyl, aryl-NH—$C_{1-6}$alkyl and $C_{1-8}$alkoxy-$C_{1-4}$alkyl. In certain instances, Z is thiazolyl, oxazolyl, isoxazoly, isothiazolyl or pyrazolyl, each of which is optionally substituted with 1-2 members selected from the group consisting of $C_{1-8}$haloalkyl, —CN, halogen, $C_{3-7}$cycloalkyl, aryl, $C_{1-8}$alkyl, aryl-NH—$C_{1-6}$alkyl and $C_{1-8}$alkoxy-$C_{1-4}$alkyl. In some occurrences, the thiazolyl is 2-thiazolyl. In the above embodiments and instances, Z is optionally substituted with 1-2 members selected from 3-chloropropyl, phenylaminomethyl, —$CH_3$, $CH_2CH_3$, —Cl, —F, —$CF_3$, —$CF_2H$, —$OCF_3$, $CH_3OCH_2$—, cyclopropyl, isopropyl and —CN. In some instances, Z is 2-thiazolyl, optionally substituted with a member selected from —F, —Cl, —CN, —$CF_3$ or —$OCF_3$.

In some embodiments of the compounds having Formula (I) or (IA), or pharmaceutically acceptable salts or solvates thereof, B is a 6-membered arylene or heteroarylene, wherein B is optionally joined to $R^7$ to form a 5- or 6-membered fused carbocyclic or heterocyclic ring having from 1-2 heteroatoms as ring members selected from O, N or S; and Z is a five-member heteroaryl whose point of indirect attachment is para to that of $R^7$.

In other embodiments of the compounds having Formula (I) or (IA), or pharmaceutically acceptable salts or solvates thereof, B is pyrrole ring, pyrazole ring, imidazole ring, pyrazine ring, oxazole ring, isoxazole ring, thiazole ring, furan ring, pyridine ring, pyrimidine ring, benzothiazole ring, purine ring, benzimidazole ring, indole ring, isoquinole ring, quinoxaline, quinoline, and Z is 2-thiazolyl, 4-thiazolyl, 5-thiazolyl.

In yet other embodiments of the compounds having Formula (I) or (IA), or pharmaceutically acceptable salts or solvates thereof, B is a divalent radical derived from 1-pyrrolyl, 2-pyrrolyl, 3-pyrrolylene, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl and Z is 2-thiazolyl, 4-thiazolyl, and 5-thiazolyl.

As noted earlier, in some embodiments, with respect to each of the above recitals respecting Formula I and/or IA, at each recital of each of the terms, the term "alkyl" by itself or as part of another substituent, means an unsubstituted, fully saturated, straight or branched chain hydrocarbon radical; the term "cycloalkyl" by itself or as part of another substituent means an unsubstituted, fully saturated, cyclic hydrocarbon radical; and the term "aryl" by itself or as part or another substituent means a monovalent monocyclic, bicyclic or polycyclic polyunsaturated aromatic hydrocarbon radical.

Subformula of Formula I

In one embodiment, the compounds of formula I or IA have a subformula (Ia):

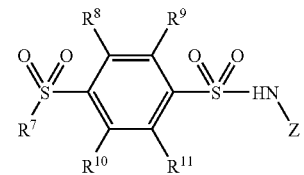

Ia wherein Z is 2-thiazolyl, 4-thiazolyl, 5-thiazolyl, oxazolyl, isoxazoly, isothiazolyl or pyrazolyl, each of which is optionally substituted with 1-2 members selected from the group consisting of $C_{1-8}$haloalkyl, —CN, halogen, $C_{3-7}$cycloalkyl, aryl, $C_{1-8}$alkyl, aryl-NH—$C_{1-6}$alkyl and $C_{1-8}$alkoxy-$C_{1-4}$alkyl; $R^7$ is aryl, aryl-$C_{1-8}$alkyl or heteroaryl-$C_{1-8}$alkyl; and $R^8$, $R^9$, $R^{10}$ and $R^{11}$ are each independently selected from the group consisting of —H, —$OR^h$, halogen, $C_{1-8}$alkyl, $C_{1-8}$haloalkyl, $C_{1-8}$haloalkoxy, and —CN. In certain instances, $R^8$, $R^9$, $R^{10}$ and $R^{11}$ are each independently selected from —F, —$CF_3$, —OH, —CN or —$CH_3$.

In another embodiment, the compounds of formula I or IA have a subformula (Ib):

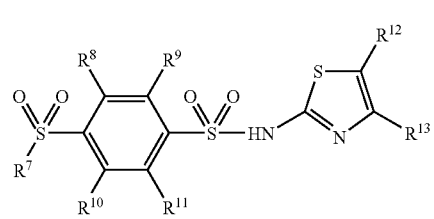

(Ib)

wherein $R^7$ is aryl, aryl-$C_{1-8}$alkyl or heteroaryl-$C_{1-8}$alkyl; $R^8$, $R^9$, $R^{10}$ and $R^{11}$ are each independently selected from the group consisting of —H, —$OR^h$, halogen, $C_{1-8}$alkyl, $C_{1-8}$haloalkyl, $C_{1-8}$haloalkoxy, and —CN; $R^{12}$ and $R^{13}$ are each independently selected from the group consisting of —H, halogen, $C_{1-4}$haloalkyl and $C_{1-4}$alkyl. In certain instances, $R^8$ and $R^{11}$ are —H and $R^9$ and $R^{10}$ are each independently —H or halogen. In other instances, $R^{12}$ and $R^{13}$ are each independently —H or halogen.

In yet another embodiment, the compounds of formula I or IA have a subformula (Ic):

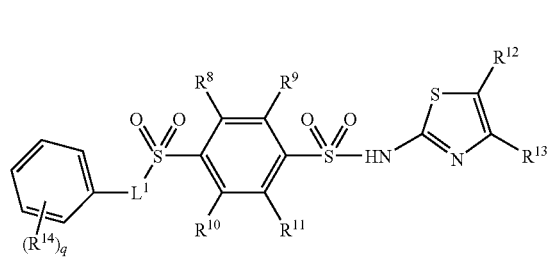

Ic wherein $R^8$, $R^9$, $R^{10}$ and $R^{11}$ are each independently selected from the group consisting of —H, halogen, $C_{1-8}$alkyl, $C_{1-8}$haloalkyl, $C_{1-8}$haloalkoxy, and —CN; $R^{12}$ and $R^{13}$ are each independently selected from the group consisting of —H, halogen, $C_{1-4}$haloalkyl and $C_{1-4}$alkyl;

$L^1$ is a bond or $C_{1-6}$alkylene, wherein one or two carbon atoms in the alkylene chain are optionally replaced by a member selected from —O—, —S—, —C(O)—, —C(O)O— or —N($R^h$)—; each $R^{14}$ is independently halogen, $C_{1-8}$alkyl, $C_{1-8}$haloalkyl and $C_{1-8}$haloalkoxy; and the subscript q is an integer of from 0-5. In one instance, $L^1$ is a bond. In certain instances, q is 1 or 2 and each $R^{14}$ is independently selected from the group consisting of —H, $C_{1-8}$alkyl, —$OR^h$, —Cl, —F, —$CF_3$ and $CF_3O$—. In other instances, $L^1$ is —$(CH_2)_r$—, wherein the subscript r is an integer of from 1-6 and one of the —$CH_2$— groups is optionally replaced by a member selected from —O—, —S—, —C(O)—, —C(O)O— or —N($R^h$)—. In some occurrences, r is 1, 2, 3 or 4. In yet other instances, $R^{12}$ and $R^{13}$ are each independently selected —H, —$CF_3$ or halogen; $R^8$ and $R^9$ are each independently selected from —H or halogen; and $R^{10}$ and $R^{11}$ are —H.

Again, in some embodiments, with respect to each of the above recitals respecting the subformula of Formula I and/or IA, at each recital of each of the terms, the term "alkyl" by itself or as part of another substituent, means an unsubstituted, fully saturated, straight or branched chain hydrocarbon radical; the term "cycloalkyl" by itself or as part of another substituent means an unsubstituted, fully saturated, cyclic hydrocarbon radical; and the term "aryl" by itself or as part or another substituent means a monovalent monocyclic, bicyclic or polycyclic polyunsaturated aromatic hydrocarbon radical.

Exemplary compounds of the present invention, having formulas I, IA, Ia, Ib or Ic, consisting of compounds, pharmaceutically acceptable salts, hydrates or solvates thereof, as set forth in Table II.

TABLE II 1. 4-(phenethylsulfonyl)-N-(thiazol-2-yl)benzenesulfonamide;
2. 4-(3-chloro-4-(trifluoromethyl)phenethylsulfonyl)-N-(thiazol-2-yl)benzenesulfonamide;
3. N-(thiazol-2-yl)-4-(3-(trifluoromethyl)phenethylsulfonyl)benzenesulfonamide;
4. 4-(4-chloro-3-(trifluoromethyl)phenethylsulfonyl)-N-(thiazol-2-yl)benzenesulfonamide;
5. 4-(4-chloro-3-(trifluoromethoxy)phenethylsulfonyl)-N-(thiazol-2-yl)benzenesulfonamide;
6. 4-(3-chloro-2-fluorophenethylsulfonyl)-N-(thiazol-2-yl)benzenesulfonamide;
7. N-(thiazol-2-yl)-4-(2-(trifluoromethyl)phenethylsulfonyl)benzenesulfonamide;
8. 4-(4-chloro-2-fluorophenethylsulfonyl)-N-(thiazol-2-yl)benzenesulfonamide;
9. N-(5-fluorothiazol-2-yl)-4-(phenethylsulfonyl)benzenesulfonamide;
10. 4-(3-fluoro-4-(trifluoromethyl)phenethylsulfonyl)-N-(5-fluorothiazol-2-yl)benzenesulfonamide;
11. 4-(3-chloro-4-(trifluoromethyl)phenethylsulfonyl)-N-(5-fluorothiazol-2-yl)benzenesulfonamide;
12. N-(5-fluorothiazol-2-yl)-4-(4-(trifluoromethyl)phenethylsulfonyl)benzenesulfonamide;
13. N-(5-fluorothiazol-2-yl)-4-(3-(trifluoromethyl)phenethylsulfonyl)benzenesulfonamide;
14. 4-(4-fluoro-3-(trifluoromethyl)phenethylsulfonyl)-N-(5-fluorothiazol-2-yl)benzenesulfonamide;
15. 4-(4-chloro-3-(trifluoromethyl)phenethylsulfonyl)-N-(5-fluorothiazol-2-yl)benzenesulfonamide;
16. N-(5-fluorothiazol-2-yl)-4-(3-(trifluoromethoxy)phenethylsulfonyl)benzenesulfonamide;
17. 4-(4-chloro-3-(trifluoromethoxy)phenethylsulfonyl)-N-(5-fluorothiazol-2-yl)benzenesulfonamide;
18. 4-(4-fluoro-3-(trifluoromethoxy)phenethylsulfonyl)-N-(5-fluorothiazol-2-yl)benzenesulfonamide;
19. 4-(3-fluoro-4-(trifluoromethyl)phenethylsulfonyl)-N-(thiazol-2-yl)benzenesulfonamide;
20. N-(thiazol-2-yl)-4-(4-(trifluoromethyl)phenethylsulfonyl)benzenesulfonamide;
21. 4-(4-fluoro-3-(trifluoromethyl)phenethylsulfonyl)-N-(thiazol-2-yl)benzenesulfonamide;
22. N-(thiazol-2-yl)-4-(3-(trifluoromethoxy)phenethylsulfonyl)benzenesulfonamide;
23. 4-(4-fluoro-3-(trifluoromethoxy)phenethylsulfonyl)-N-(thiazol-2-yl)benzenesulfonamide;
24. 3-fluoro-N-(thiazol-2-yl)-4-(4-(trifluoromethoxy)phenethylsulfonyl)benzenesulfonamide;

TABLE II-continued 25. 2-fluoro-N-(thiazol-2-yl)-4-(3-(trifluoromethoxy)phenethylsulfonyl)benzenesulfonamide;
26. 3-fluoro-N-(5-fluorothiazol-2-yl)-4-(4-(trifluoromethoxy)phenethylsulfonyl)benzenesulfonamide;
27. 2-fluoro-N-(5-fluorothiazol-2-yl)-4-(3-(trifluoromethoxy)phenethylsulfonyl)benzenesulfonamide;
28. N-(5-chlorothiazol-2-yl)-3-fluoro-4-(4-(trifluoromethoxy)phenethylsulfonyl)benzenesulfonamide;
29. N-(5-chlorothiazol-2-yl)-2-fluoro-4-(3-(trifluoromethoxy)phenethylsulfonyl)benzenesulfonamide;
30. 3-fluoro-N-(thiazol-2-yl)-4-(4-(trifluoromethyl)phenethylsulfonyl)benzenesulfonamide;
31. 2-fluoro-N-(thiazol-2-yl)-4-(3-(trifluoromethyl)phenethylsulfonyl)benzenesulfonamide;
32. 3-fluoro-N-(5-fluorothiazol-2-yl)-4-(4-(trifluoromethyl)phenethylsulfonyl)benzenesulfonamide;
33. 2-fluoro-N-(5-fluorothiazol-2-yl)-4-(3-(trifluoromethyl)phenethylsulfonyl)benzenesulfonamide;
34. N-(5-chlorothiazol-2-yl)-3-fluoro-4-(4-trifluoromethyl)phenethylsulfonyl)benzenesulfonamide;
35. N-(5-chlorothiazol-2-yl)-2-fluoro-4-(3-(trifluoromethyl)phenethylsulfonyl)benzenesulfonamide;
36. N-(5-chlorothiazol-2-yl)-4-(3-(4-(trifluoromethoxy)phenyl)propylsulfonyl)benzenesulfonamide;
37. N-(5-chlorothiazol-2-yl)-4-(4-(trifluoromethyl)benzylsulfonyl)benzenesulfonamide;
38. 4-(3-phenylpropylsulfonyl)-N-(thiazol-2-yl)benzenesulfonamide;
39. 4-(benzylsulfonyl)-N-(thiazol-2-yl)benzenesulfonamide;
40. N-(thiazol-2-yl)-4-(3-(3-(trifluoromethyl)phenyl)propylsulfonyl)benzenesulfonamide;
41. N-(thiazol-2-yl)-4-(3-(trifluoromethyl)benzylsulfonyl)benzenesulfonamide;
42. N-(5-chlorothiazol-2-yl)-4-(3-(3-(trifluoromethoxy)phenyl)propylsulfonyl)benzenesulfonamide;
43. N-(5-fluorothiazol-2-yl)-4-(3-(trifluoromethoxy)benzylsulfonyl)benzenesulfonamide;
44. N-(thiazol-2-yl)-4-(3-(4-(trifluoromethyl)phenyl)propylsulfonyl)benzenesulfonamide;
45. N-(thiazol-2-yl)-4-(4-(trifluoromethyl)benzylsulfonyl)benzenesulfonamide;
46. N-(thiazol-2-yl)-4-(4-(trifluoromethyl)benzylsulfonyl)benzenesulfonamide;
47. N-(thiazol-2-yl)-4-(4-(trifluoromethyl)benzylsulfonyl)benzenesulfonamide;
48. 4-(3-fluoro-4-(trifluoromethoxy)phenethylsulfonyl)-N-(thiazol-2-yl)benzenesulfonamide;
49. 4-(3-chloro-4-(trifluoromethoxy)phenethylsulfonyl)-N-(thiazol-2-yl)benzenesulfonamide;
50. N-(thiazol-2-yl)-4-(4-(trifluoromethoxy)phenethylsulfonyl)benzenesulfonamide;
51. 4-(3-chloro-4-(trifluoromethoxy)phenethylsulfonyl)-N-(5-fluorothiazol-2-yl)benzenesulfonamide;
52. N-(5-chlorothiazol-2-yl)-4-(4-(trifluoromethoxy)phenethylsulfonyl)benzenesulfonamide;
53. 4-(3-fluoro-4-(trifluoromethoxy)phenethylsulfonyl)-N-(5-fluorothiazol-2-yl)benzenesulfonamide;
54. N-(5-chlorothiazol-2-yl)-4-(phenethylsulfonyl)benzenesulfonamide;
55. N-(5-chlorothiazol-2-yl)-4-(3-fluoro-4-(trifluoromethyl)phenethylsulfonyl)benzenesulfonamide;
56. 4-(3-chloro-4-(trifluoromethyl)phenethylsulfonyl)-N-(5-chlorothiazol-2-yl)benzenesulfonamide;
57. N-(5-chlorothiazol-2-yl)-4-(4-(trifluoromethyl)phenethylsulfonyl)benzenesulfonamide;
58. N-(5-chlorothiazol-2-yl)-4-(3-(trifluoromethyl)phenethylsulfonyl)benzenesulfonamide;
59. N-(5-chlorothiazol-2-yl)-4-(3-(trifluoromethoxy)phenethylsulfonyl)benzenesulfonamide;
60. 4-(4-chloro-3-(trifluoromethyl)phenethylsulfonyl)-N-(5-chlorothiazol-2-yl)benzenesulfonamide;
61. N-(5-chlorothiazol-2-yl)-4-(4-fluoro-3-(trifluoromethoxy)phenethylsulfonyl)benzenesulfonamide;
62. N-(5-chlorothiazol-2-yl)-4-(3-(trifluoromethoxy)phenethylsulfonyl)benzenesulfonamide;
63. N-(5-chlorothiazol-2-yl)-4-(4-fluoro-3-(trifluoromethyl)phenethylsulfonyl)benzenesulfonamide;
64. 4-(4-chloro-3-(trifluoromethoxy)phenethylsulfonyl)-N-(5-chlorothiazol-2-yl)benzenesulfonamide;
65. 4-(phenylsulfonyl)-N-(thiazol-2-yl)benzenesulfonamide.

Compounds 1-65 set forth in Table II can be prepared by the methods described in Schemes A to F described herein below.

Included within the scope of the present invention are all stereoisomers, geometric isomers and tautomeric forms of the compounds of Formulas I, IA and Ia-Ic, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Also within the scope of the present invention are compounds of the invention that are poly- or multi-valent species, including, for example, species such as dimers, trimers, tetramers and higher homologs of the compounds of the invention or reactive analogues thereof. The poly- and multi-valent species can be assembled from a single species or more than one species of the invention. For example, a dimeric construct can be "homo-dimeric" or "heterodimeric." Moreover, poly- and multi-valent constructs in which a compound of the invention or a reactive analogue thereof, can be attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of the invention). Moreover, the framework can be derivatized with a single species of the invention or more than one species of the invention.

Moreover, the present invention includes compounds within a motif described herein, which are functionalized to afford compounds having water-solubility that is enhanced relative to analogous compounds that are not similarly functionalized. Thus, any of the substituents set forth herein can be replaced with analogous radicals that have enhanced water solubility. For example, it is within the scope of the invention to, for example, replace a hydroxyl group with a diol, or an amine with a quaternary amine, hydroxy amine or similar more water-soluble moiety. In a preferred embodiment, additional water solubility is imparted by substitution at a site not essential for the activity towards the ion channel of the compounds set forth herein with a moiety that enhances the water solubility of the parent compounds. Methods of enhancing the water-solubility of organic compounds are known in the art. Such methods include, but are not limited to, functionalizing an organic nucleus with a permanently charged moiety, e.g., quaternary ammonium, or a group that is charged at a physiologically relevant pH, e.g. carboxylic acid, amine. Other methods include, appending to the organic nucleus hydroxyl- or amine-containing groups, e.g. alcohols, polyols, polyethers, and the like. Representative examples include, but are not limited to, polylysine, polyethyleneimine, poly(ethyleneglycol) and poly(propyleneglycol). Suitable functionalization chemistries and strategies for these compounds are known in the art. See, for example, Dunn, R. L., et al., Eds. *Polymeric Drugs and Drug Delivery Systems*, ACS Symposium Series Vol. 469, American Chemical Society, Washington, D.C. 1991.

Accordingly, in a first set of embodiments, the invention provides a compound of Formula I:

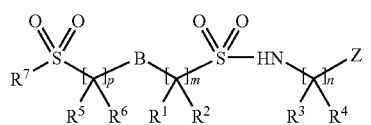

(I)

or a pharmaceutically acceptable salt or solvate thereof, wherein $R^1$, $R^2$, $R^3$, $R^4$, $R^5$ and $R^6$ are each independently selected from H, halogen, $C_{1-8}$haloalkyl, $C_{1-8}$alkyl, aryl, heteroaryl or heterocycloalkyl, wherein two or more members selected from $R^1$, $R^2$, $R^3$, $R^4$, $R^5$ and $R^6$ are optionally joined to form a 4-8-member carbocyclic or heterocyclic ring having from 1-3 heteroatoms as ring members selected from O, N or S; $R^7$ is a member selected from $C_{1-8}$alkyl, heterocycloalkyl, aryl and heteroaryl, with the proviso that $R^7$ is other than methyl, and $R^7$ is not bound to the $S(O)_2$ moiety of Formula (I) through a sulfur-nitrogen bond; wherein the aliphatic portion of $R^1$, $R^2$, $R^3$, $R^4$, $R^5$, $R^6$, $R^7$ groups is optionally substituted with from 1-3 $R^a$ substituents selected from the group consisting of —$OR^b$, =O, =$NR^b$, =N—$OR^b$, —$NR^bR^b$, —$SR^b$, -halogen, —$Si(R^b)_3$, —$OC(O)R^b$, —$C(O)R^b$, —$CO_2R^b$, —$CON(R^b)_2$, —$OC(O)N(R^b)_2$, —$NR^bC(O)R^b$, —$NR^b$—$C(O)N(R^b)_2$, —$NR^bC(O)_2R^b$, —$NR^b$—$C(NR^bR^b)$=$NR^b$, —$S(O)R^b$, —$S(O)_2R^b$, —$S(O)_2N(R^b)_2$, —$NRSO_2R^b$, $C_{1-8}$alkyl, —CN—$R^b$ and ≤$NO_2$, wherein each $R^b$ is independently H, $C_{1-8}$alkyl, aryl or heteroaryl and two $R^b$ groups when attached to the same nitrogen atom are optionally combined with the nitrogen atom to which they are attached to form a 5-6 membered ring having from 0-2 additional heteroatoms as ring members selected from O, N or S; wherein $R^b$ group is further optionally substituted with from 1-3 $R^c$ substituents selected from —$OR^d$, =O, =$NR^d$, =N—$OR^d$, —$NR^dR^d$, —$SR^d$, -halogen, —$Si(R^d)_3$, —OC(O)$R^d$, —C(O)$R^d$, —$CO_2R^d$, —$CON(R^d)_2$, —OC(O)N($R^d$)$_2$, —$NR^dC(O)R^d$, —$NR^d$—$C(O)N(R^d)_2$, —$NR^dC(O)_2R^d$, —$NR^d$—$C(NR^dR^d)$=$NR^d$, —$S(O)R^d$, —$S(O)_2R^d$, —$S(O)_2N(R^d)_2$, —$NRSO_2R^d$, $C_{1-8}$alkyl, —CN and —$NO_2$, wherein $R^d$ is —H, $C_{1-8}$alkyl or aryl and two $R^d$ groups when attached to the same nitrogen atom are optionally combined together with the nitrogen atom to which they are attached to form a 5-6 membered ring having from 0-2 additional heteroatoms as ring members selected from O, N or S; the aryl or heteroaryl moiety of $R^1$, $R^2$, $R^3$, $R^4$, $R^5$, $R^6$ and $R^7$ groups are each optionally substituted with from 1-3 $R^e$ substituents selected from halogen, —$OR^f$, —$NR^fR^f$, —$SR^f$, -halogen, —$Si(R^f)_3$, —OC(O)$^f$, —C(O)$R^f$, —$CO_2R^f$, —$CON(R^f)_2$, —OC(O)N($R^f$)$_2$, —$NR^fC(O)R^f$, —$NR^f$—C(O)N($R^f$)$_2$, —$NR^fC(O)_2R^f$, —$NR^f$—C($NR^fR^f$)=$NR^f$, —$S(O)R^f$, —$S(O)_2R^f$, —$S(O)_2NR^fR^f$, —$NRSO_2R^f$, $C_{1-8}$alkyl, —CN and —$NO_2$, $C_{1-8}$alkyl, —$N_3$, —$CH(Ph)_2$, fluoro$C_{1-4}$alkoxy, and fluoro$C_{1-4}$alkyl, wherein $R^f$ is —H, $C_{1-8}$alkyl, aryl or heteroaryl and two $R^f$ groups when attached to the same nitrogen atom are optionally combined together with the nitrogen atom to which they are attached to form a 5-6 membered ring having from 0-2 additional heteroatoms as ring members selected from O, N or S; wherein the aliphatic portion of $R^f$ group is further optionally substituted with from 1-3 $R^a$ substituents and the aromatic portion of the $R^f$ group is further optionally substituted with from 1-3 $R^g$ substituents selected from —$OR^h$, —$NR^hR^h$, —$SR^h$, -halogen, —$Si(R^h)_3$, —OC(O)$R^h$, —C(O)$R^h$, —$CO_2R^h$, —$CON(R^h)_2$, —OC(O)N($R^h$)$_2$, —$NR^hC(O)R^h$, —$NR^h$—C(O)N($R^h$)$_2$, —$NR^hC(O)_2R^h$, —$NR^h$—C($NR^hR^h$)=$NR^h$, —$S(O)R^h$, —$S(O)_2R^h$, —$S(O)_2NR^hR^h$, —$NRSO_2R^h$, —CN and —$NO_2$, $C_{1-8}$alkyl, —$N_3$, —$CH(Ph)_2$, fluoro$C_{1-4}$alkoxy, and fluoro$C_{1-4}$alkyl, wherein $R^h$ is —H or $C_{1-8}$alkyl; wherein the two $R^h$ groups when attached to the same nitrogen atom are optionally combined to form a 5-6-membered ring having from 0-2 additional heteroatoms as ring members selected from O, N or S; B is a member selected from $C_{3-7}$cycloalkylene, arylene and heteroarylene, or B is optionally joined to $R^7$ to form a fused ring, wherein the cycloalkylene is optionally substituted with from 1-3 $R^h$ substituents and the arylene or heteroarylene moiety is optionally substituted with from 1-3 $R^g$ substituents; Z is a five-membered heteroaryl having from 1-4 heteroatoms as ring members selected from O, N or S, wherein Z is optionally substituted with from 1-3 $R^e$ substituents; the subscripts m, n and p are each independently selected from the integers from 0 to 5; with the proviso when p and m are 0, n is not 0, then $R^7$ is other than aryl or heteroaryl; the terms "alkyl" and "cycloalkyl" as recited herein mean the following: "alkyl" by itself or as part of another substituent, is an unsubstituted, fully saturated, straight or branched chain hydrocarbon radical; "cycloalkyl" by itself or as part of another substituent is an unsubstituted, fully saturated, cyclic hydrocarbon radical; and "aryl" by itself or as part or another substituent is a monovalent monocyclic, bicyclic or polycyclic polyunsaturated aromatic hydrocarbon radical.

In a second set of embodiments, the present invention provides compounds of the first set, wherein m and p are not both zero.

In a third set of embodiments, the present invention provides compounds of the first and the second sets, wherein m is zero.

In the fourth set of embodiments, the invention provides compounds of the 1st and 2nd sets, wherein p is zero.

In a fifth set of embodiments, the invention provides compounds of the first set, wherein n is 0.

In a sixth set of embodiments, the invention provides compounds of the first set, wherein m and p are 0.

In a seventh set, the present invention provides compounds of the first set, wherein m and p are zero and n is 1, 2, 3, 4 or 5.

In an eighth set of embodiments, the present invention provides compounds of the first set, wherein m, n and p are zero.

In a ninth set of embodiments, the present invention provides a compound of any one of sets 1, 2, 3, 4, 5, 6, 7, and 8, wherein B is an arylene or a 6-membered heteroarylene having from 1-3 nitrogen heteroatoms as ring members, each of which is optionally substituted with 1-2 substituents selected from the group consisting of halogen, —$OR^h$, $C_{1-8}$alkyl, $C_{1-8}$haloalkyl, $C_{1-8}$haloalkoxy and —CN.

In a tenth set of embodiments, the present invention provides a compound of any one of sets 1, 2, 3, 4, 5, 6, 7, 8 and 9, wherein the arylene is substituted with halogen, —$OR^h$, $C_{1-8}$alkyl, —CN, $CF_3$ or —$OCF_3$.

In an eleventh set of embodiments, the present invention provides a compound of any one of sets 1, 2, 3, 4, 5, 6, 7, 8, 9 and 10, wherein the arylene is phenylene.

In a twelfth set of embodiments, the present invention provides a compound of any one of sets 1, 2, 3, 4, 5, 6, 7 and 8, wherein B is 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl and Z is thiazolyl.

In a thirteenth set of embodiments, the present invention provides a compound of any one of sets 1, 2, 3, 4, 5, 6, 7, 8, 9, 10, 11 and 12, wherein Z is thiazolyl, 2-thiazolyl, 3-pyrazolyl, 4-pyrazolyl, 5-pyrazolyl, isoxazolyl, imidazolyl, 1,2,4-triazolyl, 1,2,3-thiadiazolyl, 1,3,4-thiadiazolyl, 1,3,4-oxadiazolyl, 1,2,5-thiadiazol-4yl, 1,2,5-oxadiazol-4yl, 1,2,3,5-thiatriazol4yl, 1,2,3,4-thiatriazol-5yl, 1,2,3,5-oxatriazol4-yl, 1,2,3,4-oxatriazol-5yl, benzimidazolyl, benzoxazolyl, benzthiazolyl, tetrahydrobenzothiazolyl or dihydrobenzothiazolone, each of which is optionally substituted with 1-2 members selected from the group consisting of $C_{1-8}$haloalkyl, —CN, halogen, $C_{3-7}$cycloalkyl, aryl, $C_{1-8}$alkyl, aryl-NH—$C_{1-6}$alkyl and $C_{1-8}$alkoxy-$C_{1-4}$alkyl.

In a fourteenth set of embodiments, the present invention provides a compound of any one of sets 1, 2, 3, 4, 5, 6, 7, 8, 9, 10, 11 and 12, wherein Z is 2-thiazolyl, oxazolyl, isoxazoly, isothiazolyl or pyrazolyl, each of which is optionally substituted with 1-2 members selected from the group consisting of $C_{1-8}$haloalkyl, —CN, halogen, $C_{3-7}$cycloalkyl, aryl, $C_{1-8}$alkyl, aryl-NH—$C_{1-6}$alkyl and $C_{1-8}$alkoxy-$C_{1-4}$alkyl.

In a fifteenth set of embodiments, the present invention provides a compound of any one of sets 1, 2, 3, 4, 5, 6, 7, 8, 9, 10, 11 and 12, wherein Z is optionally substituted with 1-2 members selected from the group consisting of 3-chloropropyl, phenylaminomethyl, —$CH_3$, $CH_2CH_3$, —Cl, —F, —$CF_3$, —$OCF_3$, —$CF_2H$, $CH_3OCH_2$—, cyclopropyl, isopropyl and —CN.

In a sixteenth set of embodiments, the present invention provides a compound of any one of sets 1, 2, 3, 4, 5, 6, 7, 8, 9, 10, 11, 12, 13, 14 and 15, wherein $R^7$ is aryl, aryl-$C_{1-8}$alkyl or heteroaryl-$C_{1-8}$alkyl, wherein the aryl or heteroaryl moiety is optionally substituted with from 1-3 $R^e$ substituents.

In a seventeenth set of embodiments, the present invention provides a compound of any one of sets 1, 2, 3, 4, 5, 6, 7, 8, 9, 10, 11, 12, 13, 14 and 15, $R^7$ is aryl or aryl-$C_{1-8}$alkyl, optionally the aryl moiety is substituted with from 1-3 $R^e$ substituents.

In an eighteenth set of embodiments, the present invention provides a compound of any one of sets 1, 2, 3, 4, 5, 6, 7, 8, 9, 10, 11, 12, 13, 14 and 15, wherein $R^7$ is aryl or aryl-$C_{1-8}$alkyl, optionally the aryl moiety is substituted with from 1-3 members selected from the group consisting of halogen, $C_{1-8}$alkyl, $C_{1-8}$haloalkyl, $C_{1-8}$haloalkoxy, —CN and —$NO_2$.

In a nineteenth set of embodiments, the present invention provides a compound of any one of sets 1, 2, 3, 4, 5, 6, 7, 8, 9, 10, 11, 12, 13, 14 and 15, wherein $R^7$ is aryl or aryl-$C_{1-8}$alkyl, optionally the aryl moiety is substituted with from 1-3 members selected from the group consisting of —F, —Cl, —$CF_3$ and $CF_3O$—.

In a twentieth set of embodiments, the present invention provides a compound of any one of sets 1, 2, 3, 4, 5, 6, 7, 8, 9, 10, 11, 12, 13, 14 and 15, wherein $R^7$ is phenyl or phenyl-$C_{1-8}$alkyl, optionally the phenyl moiety is substituted with from 1-3 members selected from the group consisting of —F, —Cl, —$CF_3$ and $CF_3O$—.

In a 21st set embodiments, the present invention provides a compound of any one of sets 1, 2, 3, 4, 5, 6, 7, 8, 9, 10, 11, 12, 13, 14 and 15, wherein $R^7$ is aryl-$(CH_2)_q$— or heteroaryl—$(CH_2)_q$—, wherein the aryl or heteroaryl moiety is optionally substituted with from 1-3 $R^e$ substituents and the subscript q is each independently an integer of from 1-8.

In a 22nd set of embodiments, the present invention provides a compound of any one of sets 1, 2, 3, 4, 5, 6, 7 and 8, wherein B is a 6-membered arylene or heteroarylene, wherein B is optionally joined to $R^7$ to form a 5- or 6-membered fused carbocyclic or heterocyclic ring having from 1-2 heteroatoms as ring members selected from O, N or S; and Z is a five-member heteroaryl whose point of indirect attachment is para to that of $R^7$.

In a 23rd set of embodiments, the present invention provides a compound of the first set, wherein the compound has a Formula Ia:

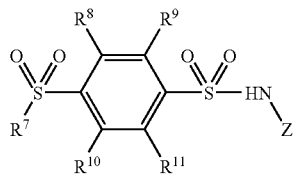

(Ia)

wherein Z is thiazolyl, oxazolyl, isoxazoly, isothiazolyl or pyrazolyl, each of which is optionally substituted with 1-2 members selected from the group consisting of $C_{1-8}$haloalkyl, —CN, halogen, $C_{3-7}$cycloalkyl, aryl, $C_{1-8}$alkyl, aryl-NH—$C_{1-6}$alkyl and $C_{1-8}$alkoxy-$C_{1-4}$alkyl; $R^7$ is aryl, aryl-$C_{1-8}$alkyl or heteroaryl-$C_{1-8}$alkyl; and $R^8$, $R^9$, $R^{10}$ and $R^{11}$ are each independently selected from the group consisting of —H, halogen, $C_{1-8}$alkyl, $C_{1-8}$haloalkyl, $C_{1-8}$haloalkoxy, and —CN.

In a 24th set of embodiments, the present invention provides a compound of the first set, wherein the compound has a Formula Ib:

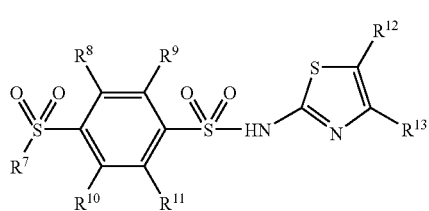

(Ib)

wherein $R^7$ is aryl, aryl-$C_{1-8}$alkyl or heteroaryl-$C_{1-8}$alkyl; $R^8$, $R^9$, $R^{10}$ and $R^{11}$ are each independently selected from the group consisting of —H, halogen, $C_{1-8}$alkyl, $C_{1-8}$haloalkyl, $C_{1-8}$haloalkoxy, and —CN; $R^{12}$ and $R^{13}$ are each independently selected from the group consisting of —H, halogen, $C_{1-4}$haloalkyl and $C_{1-4}$alkyl.

In a 25th set of embodiments, the present invention provides a compound of the 24th set, wherein $R^8$ and $R^{11}$ are —H and $R^9$ and $R^{10}$ are each independently —H or halogen.

In a 26th set of embodiments, the present invention provides a compound of the first set, wherein the compound has a Formula Ic:

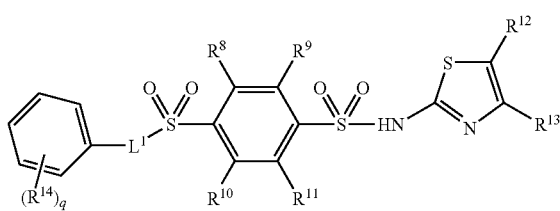

Ic wherein $R^8$, $R^9$, $R^{10}$ and $R^{11}$ are each independently selected from the group consisting of —H, halogen, $C_{1-8}$alkyl, $C_{1-8}$haloalkyl, $C_{1-8}$haloalkoxy, and —CN; $R^{12}$ and $R^{13}$ are each independently selected from the group consisting of —H, halogen, $C_{1-4}$haloalkyl and $C_{1-4}$alkyl; $L^1$ is a bond or $C_{1-6}$alkylene, wherein one or two carbon atoms in the alkylene chain are optionally replaced by a member selected from —O—, —S—, —C(O)—, —C(O)O— or —N($R^h$)—; each $R^{14}$ is independently halogen, $C_{1-8}$alkyl, $C_{1-8}$haloalkyl and $C_{1-8}$haloalkoxy; and the subscript q is an integer of from 0-5.

In a 27th set of embodiments, the present invention provides a compound of the 26th set, wherein q is 2 and each $R^{14}$ is independently selected from the group consisting of —H, —Cl, —F, —CF$_3$ and CF$_3$O—.

In a 28th set of embodiments, the present invention provides a compound of the 26th or the 27th set, wherein $L^1$ is —(CH$_2$)$_r$—, wherein the subscript r is an integer of from 1-6 and one of the —CH$_2$— groups is optionally replaced by a member selected from —O—, —S—, —C(O)—, —C(O)O— or —N($R^h$)—.

In a 29th set of embodiments, the present invention provides a compound of the 26th or the 27th set, wherein $L^1$ is a bond.

In a 30th set of embodiments, the present invention provides a compound of any of sets 24-29, wherein $R^{12}$ and $R^{13}$ are each independently selected —H or halogen; $R^8$ and $R^9$ are each independently selected from —H or halogen; and $R^{10}$ and $R^{11}$ are —H.

In a 31st set of embodiments, the present invention provides N-thiazol-2-yl)-4-(4-(trifluoromethyl)phenethylsulfonyl)benzenesulfonamide or 4-(phenylsulfonyl)-N-(thiazol-2-yl)benzenesulfonamide.

In a 32nd set of embodiments, the present invention provides a compound of any of sets 1-31, wherein the compound has inhibitory activity against a voltage-gated sodium channel.

In a 33rd set of embodiments, the present invention provides a pharmaceutical composition comprising a compound of any of sets 1-32 and a pharmaceutically acceptable excipient.

In a 34th set of embodiments, the present invention provides a method of modulating activity of a sodium channel in a subject, wherein said method comprising: administering to said subject in need thereof an effective amount of a compound of any of sets 1-32 to modulate the activity of a sodium channel.

In a 35th set of embodiments, the present invention provides a method for treating, preventing or ameliorating pain or seizures in a subject, wherein said method comprising: administering to said subject a therapeutically effective amount of a compound of any of sets 1-32 to treat, prevent or ameliorate pain or seizures.

In a 36th set of the present invention provides a method of the 35th set for treating, preventing or ameliorating pain or seizures in a subject, wherein said pain is selected from the group consisting of postoperative pain, osteoarthritis pain, pain associated with metastatic cancer, neuropathy secondary to metastatic inflammation, trigeminal neuralgia, glossopharangyl neuralgia, adiposis dolorosa, burn pain, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, pain following stroke, thalamic lesions, radiculopathy, and other forms of neuralgic, neuropathic, and idiopathic pain syndromes.

With respect to these 36 sets of embodiments, at each recital of each of the terms, the term "alkyl" by itself or as part of another substituent, means an unsubstituted, fully saturated, straight or branched chain hydrocarbon radical, the term "cycloalkyl" by itself or as part of another substituent means an unsubstituted, fully saturated, cyclic hydrocarbon radical, and the term "aryl" by itself or as part or another substituent means a monovalent monocyclic, bicyclic or polycyclic polyunsaturated aromatic hydrocarbon radical.

II. Preparation of the Compounds

Compounds of the present invention can be prepared using readily available starting materials or known intermediates. The synthetic schemes set forth below provide exemplary synthetic pathways for the preparation of compounds of the invention.

II.a. General Procedure for Synthesizing Sulfone/Sulfonamide-Containing Compounds A general route to sulfone/sulfonamide-containing compounds of the invention is shown in Scheme A.

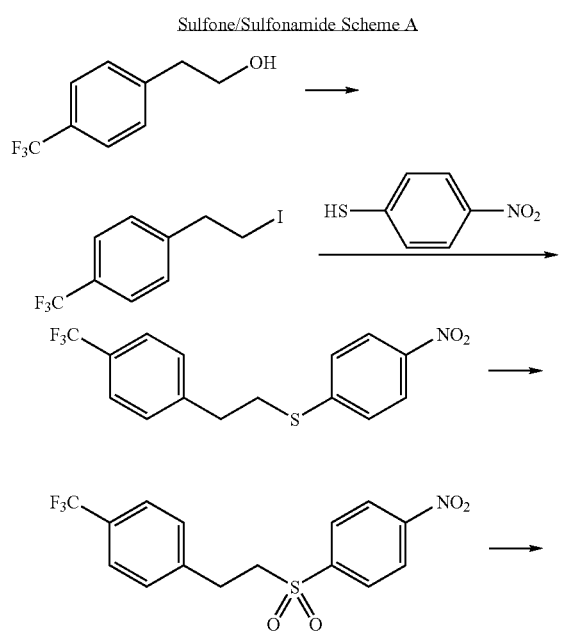

Further descriptions of this synthesis are provided in the Examples section.

An alternate route to sulfone/sulfonamide-containing compounds of the invention is provided in Scheme B.

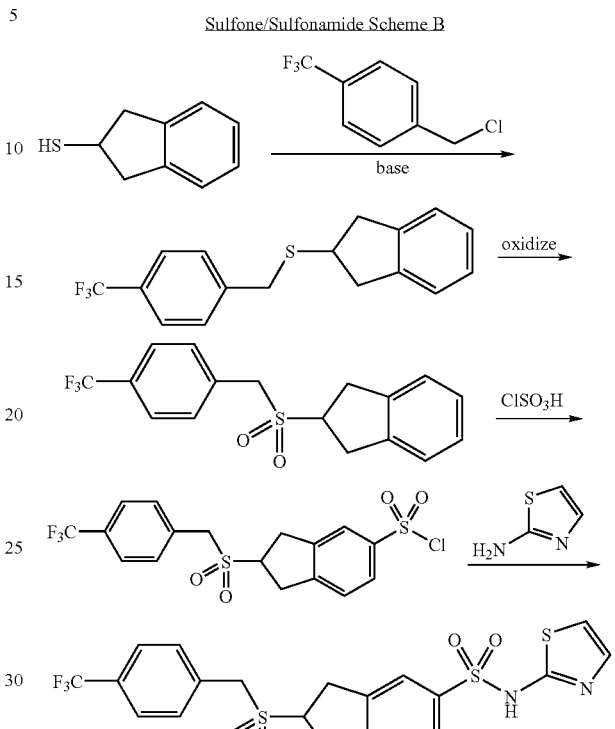

Another route to sulfone/sulfonamide-containing compounds of the invention is set forth in Scheme C:

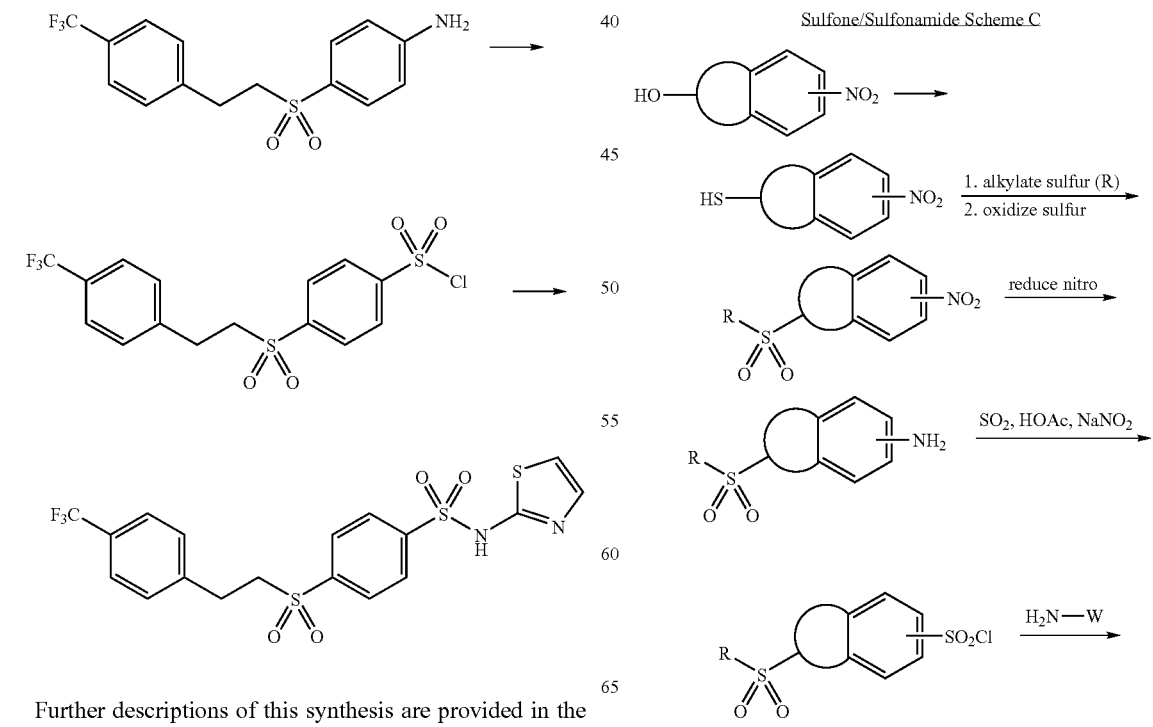

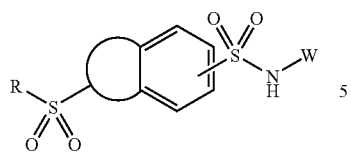

Another route to sulfone/sulfonamide-containing compounds of the invention is set forth in Scheme D:

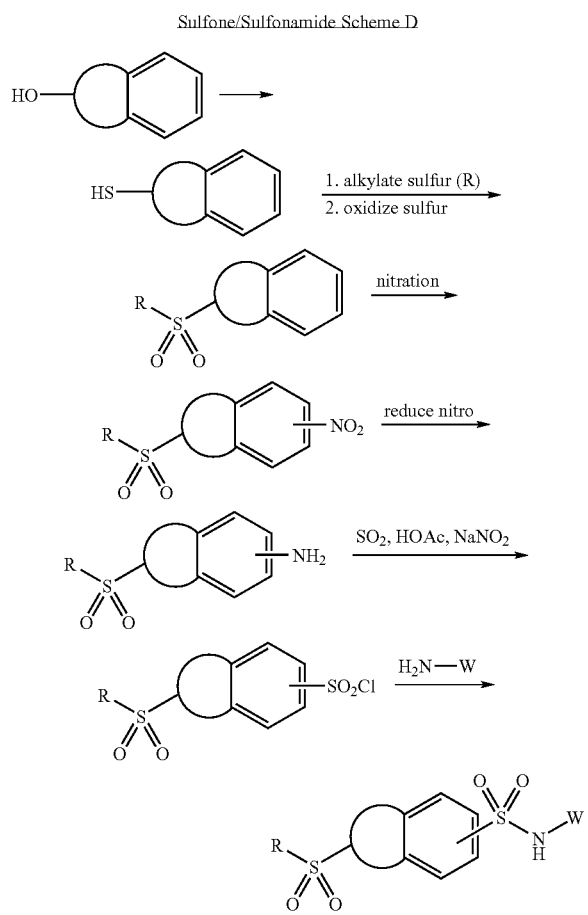

A further route to sulfone/sulfonamide-containing compounds of the invention is set forth in Scheme E:

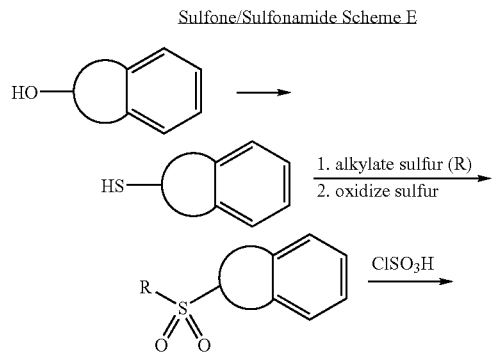

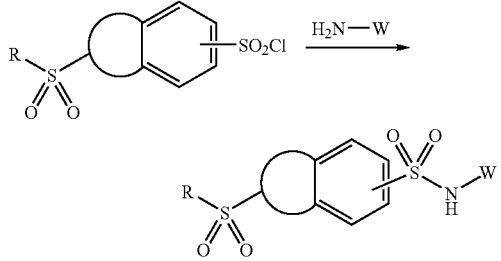

A further route to sulfone/sulfonamide-containing compounds of the invention is set forth in Scheme F:

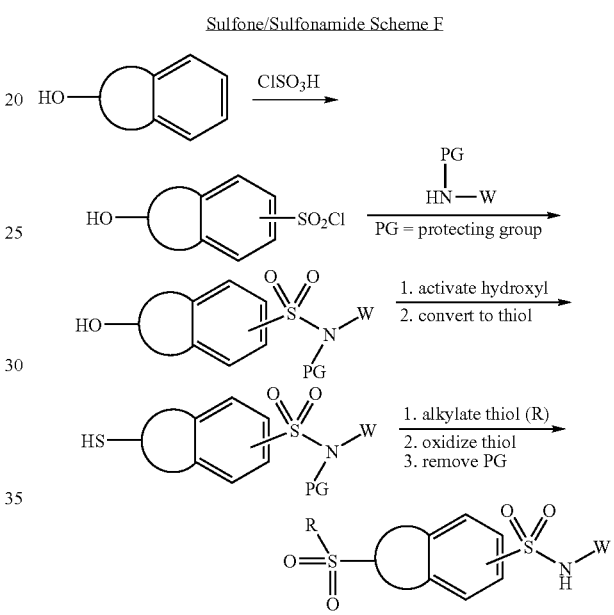

III. Assays for Blockers of Voltage-Dependent TTX-Sensitive Sodium Channels

The activity of sodium channels can be assessed using a variety of in vitro assays, including but not limited to, measuring ion flux, measuring transmembrane potential, and/or measuring ionic current. Measurement of ionic fluxes can be accomplished by measuring changes in the concentration of the permeant species or by tracking the movement of small amounts of an appropriately permeant radioactive tracer. Transmembrane potential can be assessed with voltage-sensitive fluorescent dyes or, more sensitively, with electrophysiological methods.

Determination of the effectiveness of compounds as ex vivo blockers of sodium channels can be assessed by the inhibition of compound action potential propagation in isolated nerve preparations (Kourtney and Stricharz, LOCAL ANESTHETICS, Springer-Verlag, New York, 1987). A number of experimental models in the rat are appropriate for assessing the in vivo efficacy of the compounds of the invention. For example, the neuropathic pain model produced by the tight ligation of spinal nerves, described by Kim et al., *Pain,* 50: 355-363 (1992), can be used to experimentally determine the effect of the compounds of the invention in an in vivo model of pain. Mechanical sensitivity can also be assessed using a procedure described by Chaplan et al., *J. Neurosci. Methods,* 53: 55-63 (1994). Other assays of use are known to those of skill in the art.

Modulators of TTX-sensitive sodium channels can be tested using biologically active recombinant channels, or naturally occurring TTX-sensitive sodium channels, or by using native cells, like neurons expressing a TTX-sensitive sodium current. TTX-sensitive sodium channels can be isolated, co-expressed or expressed in a cell, or expressed in a membrane derived from a cell. In such assays, TTX-sensitive sodium channels are generally expressed alone to form a homomeric sodium channel or may be co-expressed with a second subunit (e.g., an auxiliary beta subunit) so as to form a heteromeric sodium channel. The TTX-sensitive sodium channels are stably expressed in HEK-293 cells, an example of an effective mammalian expression system.

Modulation can be tested using one of the in vitro or in vivo assays described above. Samples or assays that are treated with a potential sodium channel inhibitor are compared to control samples without the test compound, to examine the extent of modulation. Control samples (untreated with inhibitors) are assigned a relative sodium channel activity value of 100. Inhibition of TTX-sensitive sodium channels is achieved when the sodium channel activity value relative to the control is less than 70%, preferably less than 40% and still more preferably, less than 30%. Compounds that decrease the flux of ions will cause a detectable decrease in the ion current density by decreasing the probability of a TTX-sensitive sodium channel being open, by decreasing conductance through the channel, decreasing the number of channels, or decreasing the expression of channels.

Changes in ion flux may be assessed by determining changes in polarization (i.e., electrical potential) of the cell or membrane expressing the sodium channel. A preferred means to determine changes in cellular polarization is by measuring changes in current or voltage with the voltage-clamp and patch-clamp techniques, using the "cell-attached" mode, the "inside-out" mode, the "outside-out" mode, the "perforated patch" mode, the "whole cell" mode or other means of controlling or measuring changes in transmembrane potential (see, e.g., Ackerman et al., *New Engl. J. Med.*, 336: 1575-1595 (1997)). Whole cell currents are conveniently determined using the standard methodology (see, e.g., Hamill et al., *Pflugers. Archiv.* 391: 85 (1981). Other known assays include: radiotracer flux assays and fluorescence assays using voltage-sensitive dyes (see, e.g., Vestergarrd-Bogind et al., *J. Membrane Biol.* 88: 67-75 (1988); Daniel et al., *J. Pharmacol. Meth.* 25: 185-193 (1991); Holevinsky et al., *J. Membrane Biology* 137: 59-70 (1994)). Assays for compounds capable of inhibiting or increasing sodium flux through the channel proteins can be performed by application of the compounds to a bath solution in contact with and comprising cells having a channel of the present invention (see, e.g., Blatz et al., *Nature* 323: 718-720 (1986); Park, *J. Physiol.* 481: 555-570 (1994)). Generally, the compounds to be tested are present in the range from about 1 nM to about 100 mM, preferably from about 1 nM to about 30 µM. In an exemplary embodiment, the compounds to be tested are present in the range from about 1 nM to about 3 µM.

The effects of the test compounds upon the function of the channels can be measured by changes in the electrical currents or ionic flux or by the consequences of changes in currents and flux. Changes in electrical current or ionic flux are measured by either increases or decreases in flux of ions such as sodium or guanidinium ions (see U.S. Pat. No. 5,688,830). The cations can be measured in a variety of standard ways. They can be measured directly by concentration changes of the ions or indirectly by membrane potential or by using radioactive ions. Consequences of the test compound on ion flux can be quite varied. Accordingly, any suitable physiological change can be used to assess the influence of a test compound on the channels of this invention. The effects of a test compound can be measured by a toxin-binding assay. When the functional consequences are determined using intact cells or animals, one can also measure a variety of effects such as transmitter release, hormone release, transcriptional changes to both known and uncharacterized genetic markers, changes in cell metabolism such as cell growth or pH changes, and changes in intracellular second messengers such as $Ca^{2+}$, or cyclic nucleotides.

High throughput screening (HTS) is of use in identifying promising candidate compounds of the invention. Physiologically, sodium channels open and close on a millisecond timescale. To overcome the short time in which channels are open the HTS assay can be run in the presence of an agent that modifies the gating of the channel, (e.g., pyrethroids, alpha-scorpion toxins, beta-scorpion toxins, batrachotoxin, etc). These agents modify the gating of sodium channels and keep the pore open for extended periods of time. In addition, while sodium channels are primarily selective for sodium, other ionic species can permeate the channel.

The specificity and effect of the TTX-sensitive sodium channel blocking agents of the invention can also be assayed against non-specific blockers of sodium channels, such as tetracaine, mexilitine, and flecainide.

IV Pharmaceutical Compositions of VGSC Inhibitors

In another aspect, the present invention provides pharmaceutical compositions comprising/including a pharmaceutically acceptable excipient and a compound of the invention described herein or a pharmaceutically acceptable salt or solvate thereof. In an exemplary embodiment, the present invention provides a pharmaceutical formulation comprising a compound described herein. In one embodiment, the compound has any of Formulas I, IA, Ia, Ib and Ic.

Formulation of the Compounds (Compositions)

The compounds of the present invention can be prepared and administered in a wide variety of oral, parenteral and topical dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and either a compound described herein, or a pharmaceutically acceptable salt of a compound described herein.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

V. Methods for Inhibiting Ion Flow in VGSC

In yet another aspect, the present invention provides methods for decreasing ion flow through voltage gated sodium channels in a cell, comprising/including contacting a cell containing the target ion channels with a sodium channel-inhibiting amount of a compound described herein. In one embodiment, the method includes contacting a cell containing the target ion channels with a sodium channel-inhibiting amount of a compound of any of Formulas I, IA, Ia, Ib and Ic.

The methods provided in this aspect of the invention are useful for the diagnosis of conditions that can be treated by inhibiting ion flux through voltage gated sodium channels, or for determining if a patient will be responsive to therapeutic agents, which act by inhibiting sodium channels.

In a still another aspect, the present invention provides a method of modulating the activity of a sodium channel in a subject. This method comprises administering to a subject an amount of a compound according a formula described herein sufficient to modulate said activity. In an exemplary embodiment, the method comprises administering to a subject an amount of a compound described herein sufficient to modulate said activity. This method comprises administering to a subject an amount of a compound according to a formula described herein sufficient to modulate said activity. In an exemplary embodiment, the method comprises administering to a subject an amount of a compound set forth in Table II, or a pharmaceutically acceptable salt or solvate thereof, sufficient to modulate the activity. In another embodiment, the method includes administering to a subject an amount of sufficient to modulate the activity. Methods of detecting and amplifying modulation of a sodium channel are generally known in the art.

VI. Methods for Treating Conditions Mediated by VGSC

The compounds of formula (II), being sodium channel modulators, are potentially useful in the treatment of a range of disorders. The treatment of pain, particularly acute pain, chronic pain, visceral pain, inflammatory pain and neuropathic pain, is a preferred use.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-teen pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a hightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
heart and vascular pain, including pain caused by angina, myocardical infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders; and orofacial pain, including dental pain, otic pain, burning mouth syndrome and temporomandibular myofascial pain.

In still another aspect, the present invention provides a method for the treatment of a disorder or condition through inhibition of a voltage gated sodium channel. In this method, a subject in need of such treatment is administered an effective amount of a compound described herein and/or according to a formula described herein. In a preferred embodiment, the compounds provided herein are used to treat a disorder or condition by inhibiting an ion channel of the VGSC family.

In one aspect, the present invention provides a method of ameliorating or alleviating a condition in a subject. The condition can be a member selected from pain, irritable bowel syndrome, Crohn's disease, epilepsy, seizures multiple sclerosis, bipolar depression and tachy-arrhythmias. The method includes administering to the subject an amount of the compound described herein sufficient to ameliorate or alleviate the condition. In one embodiment, the compound has any of Formulas I, IA, Ia, Ib and Ic. In an exemplary embodiment, the condition is pain, and the pain can be a member selected from acute pain, chronic pain, visceral pain, inflammatory pain and neuropathic pain. Exemplary aspects of this method are described in greater detail herein.

In another aspect, the present invention provides a method for the treatment of a disorder or condition through inhibition of a voltage gated sodium channel. In this method, a subject in need of such treatment is administered an effective amount of a compound described herein and/or according to a formula described herein or any of sets 1 to 36. In one embodiment, the compound has any of Formulas I, IA, Ia, Ib and Ic. In a preferred embodiment, the compounds provided herein are used to treat a disorder or condition by inhibiting an ion channel of the VGSC family.

The compounds provided herein are useful as sodium channel inhibitors and find therapeutic utility via inhibition of VGSCs in the treatment of diseases or conditions. The sodium channels that are typically inhibited are described herein as VGSCs such as the $Na_v1.1$ channel.

The compounds of the invention are particularly preferred for use in the treating, preventing or ameliorating pain or seizures. The method includes administering to a patient in need of such treatment, a therapeutically effective amount of a compound described herein and/or according to a formula described herein, or a pharmaceutically acceptable salt or solvate thereof. In one embodiment, the compound has any of Formulas I, IA, Ia, Ib aired Ic.

The compounds, compositions and methods of the present invention are of particular use in treating pain, including both inflammatory and neuropathic pain. Exemplary forms of pain treated by a compound of the invention include, postoperative pain, osteoarthritis pain, pain associated with metastatic cancer, neuropathy secondary to metastatic inflammation, trigeminal neuralgia, glossopharangyl neuralgia, adiposis dolorosa, burn pain, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, pain following stroke, thalamic lesions, radiculopathy, and other forms of neuralgic, neuropathic, and idiopathic pain syndromes.

Idiopathic pain is pain of unknown origin, for example, phantom limb pain. Neuropathic pain is generally caused by injury or infection of the peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies.

Moreover, any VGSC inhibitory substance possessed of satisfactory VGSC modulating activity coupled with favorable intracranial transfer kinetics and metabolic stability is expected to show efficacy in central nervous system (CNS) diseases and disorders such as central nervous system ischemia, central nervous system trauma (e.g. brain trauma, spinal cord injury, whiplash injury, etc.), epilepsy, seizures, neurodegenerative diseases (e.g. amyotrophic lateral sclerosis (ALS), Alzheimer's disease, Huntington's chorea, Parkinson's disease, diabetic neuropathy, etc.), vascular dementia (e.g. multi-infarct dementia, Binswanger's disease, etc.), manic-depressive psychosis, depression, schizophrenia, chronic pain, trigeminal neuralgia, migraine, ataxia, bipolar disorder, spasticity, mood disorders, psychotic disorders, hearing and vision loss, age-related memory loss, learning deficiencies, anxiety and cerebral edema.

In treatment of the above conditions, the compounds utilized in the method of the invention are administered at the initial dosage of about 0.001 mg/kg to about 1000 mg/kg daily. A daily dose range of about 0.1 mg/kg to about 100 mg/kg is more typical. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day, if desired.

In one embodiment, the present invention provides a compound as described herein or a compound of any of sets 1-36 above, or a pharmaceutically acceptable salt or solvate thereof, for use as a medicament. In one embodiment, the compound has any of Formulas I, IA, Ia, Ib and Ic.

In another embodiment, the present invention provides a compound as described herein or a compound of any of embodiment sets 1-36 above, or a pharmaceutically acceptable salt or solvate thereof, for use in the treatment of pain, irritable bowel syndrome, Crohn's disease, epilepsy, seizures, multiple sclerosis, bipolar depression and tachy-arrhythmias. In one embodiment, the compound has any of Formulas I, IA, Ia, Ib and Ic. In certain instances, the pain includes, but are not limited to, acute pain, chronic pain, visceral pain, inflammatory pain and neuropathic pain.

In yet another embodiment, the present invention provides a use of a compound as described herein or a compound of any of embodiments sets 1-36 above, or a pharmaceutically acceptable salt or solvate thereof, in the manufacture of a medicament for the treatment of pain, irritable bowel syndrome, Crohn's disease, epilepsy, seizures, multiple sclerosis, bipolar depression and tachy-arrhythmias. In certain instances, the pain includes, but are not limited to, acute pain, chronic pain, visceral pain, inflammatory pain and neuropathic pain. In one embodiment, the compound has any of Formulas I, IA, la, Ib and Ic.

Combination Therapy

Sodium channel modulators may be usefully combined with another pharmacologically active compound, or with two or more other pharmacologically active compounds, particularly in the treatment of pain. For example, a sodium channel modulator, particularly a compound of formula (I), or a pharmaceutically acceptable salt or solvate thereof, as defined above, may be administered simultaneously, sequentially or separately in combination with one or more agents selected from:

(1) an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

(2) a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

(3) a barbiturate sedative, e.g. amobarbital, aprobarbital, butabarbital, butabital, mephobarbital, metharbital, methohexital, pentobarbital, phenobartital, secobarbital, talbutal, theamylal or thiopental;

(4) a benzodiazepine having a sedative action, e.g. chlordiazepoxide, clorazepate, diazepam, flurazepam, lorazepam, oxazepam, temazepam or triazolam;

(5) an $H_1$ antagonist having a sedative action, e.g. diphenhydramine, pyrilamine, promethazine, chlorpheniramine or chlorcyclizine;

(6) a sedative such as glutethimide, meprobamate, methaqualone or dichloralphenazone;

(7) a skeletal muscle relaxant, e.g. baclofen, carisoprodol, chlorzoxazone, cyclobenzaprine, methocarbamol or orphrenadine;

(8) an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

(9) an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl)quinazoline;

(10) a tricyclic antidepressant, e.g. desipramine, imipramine, amitriptyline or nortriptyline;

(11) an anticonvulsant, e.g. carbamazepine, lamotrigine, topiratmate or valproate;

12l) a tachykinin (NK) antagonist, particularly an NK-3, NK-2 or NK-1 antagonist, e.g. (αR,9R)-7-[3,5-bis(trifluoromethybenzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

(13) a muscarinic antagonist, e.g. oxybutynin, tolterodine, propiverine, tropsium chloride, darifenacin, solifenacin, temiverine and ipratropium;

(14) a COX-2 selective inhibitor, e.g. celecoxib, rofecoxib, parecoxib, valdecoxib, deracoxib, etoricoxib, or lumiracoxib;

(15) a coal-tar analgesic, in particular paracetamol;

(16) a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

(17) a vanilloid receptor agonist (e.g. resinferatoxin) or antagonist (e.g. capsazepine);

(18) a beta-adrenergic such as propranolol;

(19) a local anaesthetic such as mexiletine;

(20) a corticosteroid such as dexamethasone;

(21) a 5-HT receptor agonist or antagonist, particularly a $5\text{-HT}_{1B/1D}$ agonist such as eletriptan, sumatriptan, naratriptan, zolmitriptan or rizatriptan;

(22) a $5\text{-HT}_{2A}$ receptor antagonist such as R(+)-alpha-(2,3-dimethoxy-phenyl)-1-[2-(4-fluorophenylethyl)]-4-piperidinemethanol (MDL-100907);

(23) a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

(24) Tramadol®;

(25) a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

(z) an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

(26) a cannabinoid;

(27) metabotropic glutamate subtype 1 receptor (mGluR1) antagonist;

(28) a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

(29) a noradrenaline (norepinephrine) reuptake inhibitor, such as maprotiline, lofepramine, mirtazepine, oxaprotiline, fezolamine, tomoxetine, mianserin, buproprion, buproprion metabolite hydroxybuproprion, nomifensine and viloxazine (Vivalan®), especially a selective noradrenaline reuptake inhibitor such as reboxetine, in particular (S,S)-reboxetine;

(30) a dual serotonin-noradrenaline reuptake inhibitor, such as venlafaxine, venlafaxine metabolite 0-desmethylvenlafaxine, clomipramine, clomipramine metabolite desmethylclomipramine, duloxetine, milnacipran and imipramine;

(31) an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl) butyl]thio]-6-(trifluoromethyl)-3pyridinecarbonitrile, 2-[[(1R, 3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

(32) an acetylcholinesterase inhibitor such as donepezil;

(33) a prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl]benzoic acid;

(34) a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870,

(35) a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl),1,4-benzoquinone (CV-6504);

(36) a sodium channel blocker, such as lidocaine;

(37) a 5-HT3 antagonist, such as ondansetron;

and the pharmaceutically acceptable salts and solvates thereof.

EXAMPLES

The following examples are offered to illustrate, but not to limit the claimed invention. In the examples below, unless otherwise stated, temperatures are given in degrees Celsius ° C.); operations were carried out at room or ambient temperature (typically a range of from about 18-25° C.; evaporation of solvent was carried out using a rotary evaporator under reduced pressure (typically, 4.5-30 mmHg) with a bath temperature of up to 60° C.; the course of reactions was typically followed by TLC and reaction times are provided for illustration only; melting points are uncorrected; products exhibited satisfactory $^1$H-NMR and/or LC/MS data and yields are provided for illustration only. The following conventional abbreviations are also used: mp (melting point), L (liter(s)), mL (milliliters), mmol (millimoles), g (grams), mg (milligrams), min (minutes), LC-MS (liquid chromatography-mass spectrometry) and h (hours), PS (polystyrene), DIE (diisopropylethylamine).

Example 1

Synthesis of N-thiazol-2-yl-4-[2-(4-trifluoromethyl-phenyl)-ethanesulfonyl]-benzenesulfonamide 1.a. Synthesis of 1-(2-iodo-ethyl)-4-trifluoromethyl-benzene

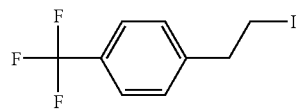

To 4-(trifluoromethyl)phenyl alcohol (5.0 g, 0.026 mol) in methylene chloride (30 mL, 0.5 mol) at 0° C. was added triethylamine (5.13 mL, 0.0368 mol) followed by methanesulfonyl chloride (3.92 g, 0.0342 mol). After stirring from 0° C. to room temperature for 3 hours, the reaction mixture was washed with 1N HCl, saturated $NaHCO_3$, water, brine and dried over anhydrous sodium sulfate. To the crude product in acetone (50 mL, 0.7 mol) was added sodium iodide (5.9 g, 0.039 mol). The reaction mixture was stirred at 55° C. overnight, filtered and the solid washed with acetone. The filtrate was concentrated, dissolved in $Et_2O$ (100 mL), washed with water, brine and dried over anhydrous sodium sulfate to give 7.51 g of brown liquid.

1.b. Synthesis of (4-nitrophenyl)(4-(trifluoromethyl) phenethyl)sulfane

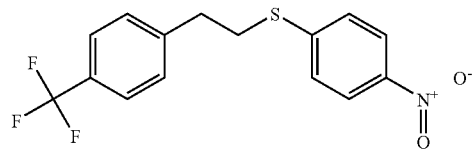

To a solution of 1-(2-iodo-ethyl)-4-trifluoromethyl-benzene (7.51 g, 25.0 mmol), triethylamine (3.84 mL, 27.5 mmol) in THF (100 mL) was added p-nitrothiophenol (4.85 g, 25.0 mmol). The reaction was stirred at room temperature for two days, diluted with EtOAc, washed with water, saturated $NaHCO_3$, $H_2O$, brine and dried over anhydrous sodium sulfate. The compound was purified on silica gel (hexane-EtOAc) to give 7.24 g of a yellow solid.

$^1$H NMR ($CDCl_3$): δ 3.11 (2H, t, J=7.7. Hz), 3.34 (2H, t, J=7.7 Hz), 7.35 (4H, m), 7.62 (2H, d, J=7.9 Hz), 8.17 (2H, d, J=8.3 Hz).

1.c. Synthesis of 1-nitro-4-(4-(trifluoromethyl)phenethylsulionyl)benzene

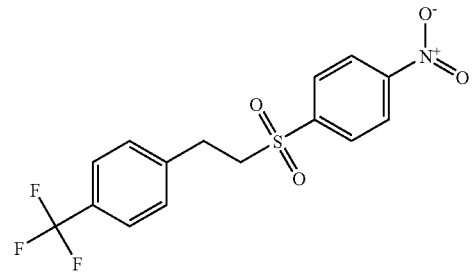 [SMILES: O=[N+]([O-])c1ccc(S(=O)(=O)CCc2ccc(C(F)(F)F)cc2)cc1]

To (4-nitrophenyl)(4-(trifluoromethyl)phenethyl)sulfane (4.0 g, 0.012 mol) in methylene chloride (100 mL, 2 mol) at 0° C. was added m-chloroperbenzoic acid (7.5 g, 0.030 mol). After stirring overnight at room temperature, the reaction mixture was diluted with EtOAc, washed with 1N NaOH, H$_2$O, brine, dried over anhydrous sodium sulfate and purified on silica gel (hexane-EtOAc) to give 3.99 g of a white solid.

$^1$H NMR (CDCl$_3$): δ 3.18-3.23 (2H, m), 3.44-3.50 (2H, m), 7.29 (2H, d, J=7.6 Hz), 7.57 (2H, d, J=8.1 Hz), 8.15 (2H, d, J=8.8 Hz), 8.44 (2H, d, J=8.8 Hz).

1.d. Synthesis of 4-[2-(4-trifluoromethyl-phenyl)-ethanesulonyl]-phenylamine

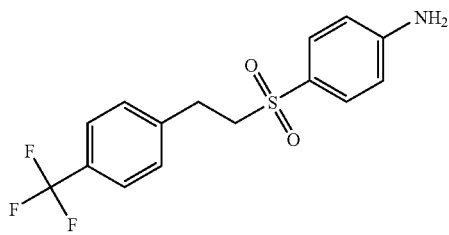 [SMILES: Nc1ccc(S(=O)(=O)CCc2ccc(C(F)(F)F)cc2)cc1]

To 1-nitro-4-(4-(trifluoromethyl)phenethylsulfonyl)benzene (3.99 g, 0.0111 mol) in methanol (84 mL, 2.1 mol) under argon was added 10% palladium on carbon. The reaction mixture was stirred under hydrogen overnight, filtered over Celite, concentrated and purified on silica gel (hexane-EtOAc) to give 3.13 g of a white solid. LCMS: M+330.

1.e. Synthesis of 4-[2-(4-trifluoromethyl-phenyl)-ethanesulfonyl]-benzenesulfonyl chloride

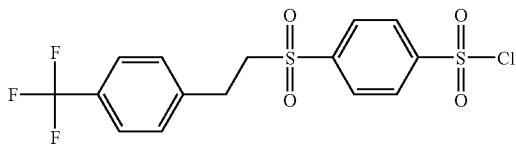 [SMILES: O=S(=O)(Cl)c1ccc(S(=O)(=O)CCc2ccc(C(F)(F)F)cc2)cc1]

Sodium nitrite (0.330 g, 0.00478 mol) in water (1.6 mL, 0.090 mol) was added to a solution of 4-[2-(4-trifluoromethyl-phenyl)-ethanesulfonyl]-phenylamine (1.50 g, 0.00455 mol) in concentrated hydrogen chloride (7.8 mL) cooled at −5° C. Acetonitrile was added to help dissolve the solid. The solution was stirred at −5° C. for 2 hours. Copper (II) chloride (0.61 g, 0.0046 mol) was added to 25% SO$_2$ in acetic acid (12.9 mL, 0.228 mol) cooled at −10° C. The suspension of diazonium salt was added. The reaction mixture was stirred from −10° C. to room temperature for 3 h. The reaction mixture was poured onto ice-water then filtered. The solid was washed with water to give a paste. The paste was dissolved in dichloromethane and dried over anhydrous sodium sulfate to give 1.29 g of a red brown solid.

1.f. Synthesis of N-thiazol-2-yl-4-[2-(4-trifluoromethyl-phenyl)-ethanesulfonyl]-benzenesulfonamide

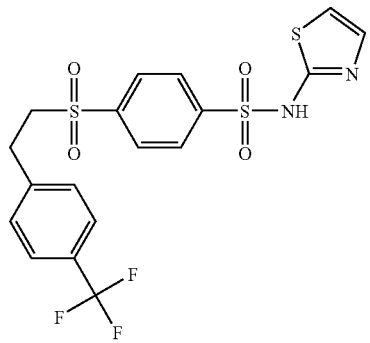 [SMILES: O=S(=O)(CCc1ccc(C(F)(F)F)cc1)c1ccc(S(=O)(=O)Nc2nccs2)cc1]

To 4-[2-(4-Trifluoromethyl-phenyl)-ethanesulfonyl]-benzenesulfonyl chloride (1288 mg, 0.003120 mol) and 2-aminothiazole (0.31 g, 0.0031 mol) was added pyridine (20 mL). After stirring overnight, the reaction mixture was concentrated, dissolved in DMSO (4 mL) and purified by reversed phase chromatography (Phenomenex 250×30 mm 15 micron C18 column. 40 mL/min. Gradient 85% A to 100% B over 25 min. Solvent A: 7800 water/200 acetonitrile/8 TFA. Solvent B: 7200 acetonitrile/800 water/8 TFA). The compound was further purified on silica gel (CHCl$_3$-10% MeOH in CHCl$_3$) to give 94 mg of a light brown solid. LCMS: M+477.

Example 2

Synthesis of 4-(phenylsulfonyl)-N-(thiazol-2-yl)benzenesulfonamide 2.a. Synthesis of 4-(N-thiazol-2-ylsulfamoyl)benzene-1-sulfonyl chloride

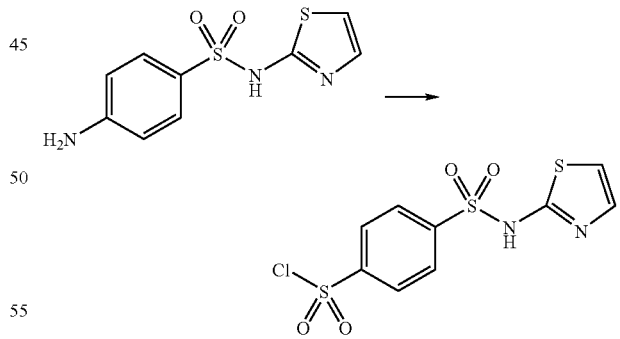

This intermediate is described in our earlier patent. "Aryl sulfonamide compound sodium channel inhibitors, and their therapeutic use." PCT Int. Appl. (2007) WO 2007056099, the application is incorporated herein by reference.

2.b. Synthesis of 4-(phenylsulfonyl)-N-(thiazol-2-yl)benzenesulfonamide 4-(N-thiazol-2-ylsulfamoyl)benzene-1-sulfonyl chloride (0.339 g, 0.00100 mol) was mixed in tetrahydrofuran (15 mL)

and cooled to −78° C. Phenylmagnesium bromide (0.363 g, 0.002 mol) solution in THF (1M) was added to the reaction in a dropwise manner. The reaction was allowed to stir 1 hour while warming to room temperature. A second portion of phenyl magnesium bromide solution (0.181 g, 0.001 mol) was added to the reaction mixture. The reaction mixture was then stirred for 18 hours then quenched with saturated ammonium chloride solution. The organic phase was separated and dried over magnesium sulfate. The organic phase was evaporated to a residue and purified by column chromatography (12 g silica gel ISCO column, hexanes to ethyl acetate gradient elution). Product fractions were combined and rotary evaporated to give 15.7 mg of product as white crystals. LCMS: Rt=1.30 min, MS m/z 380.6 [MH]+.

Example 3 provides methods for testing the efficacy of the compounds of the invention.

Compounds 1-65 in Table II were prepared using the methods analogous to those of Examples 1 and 2.

Example 3

3.a. Cell Line Construction and Maintenance

Human Embryonic Kidney (HEK) cells were transfected with hSCN3A or hSCN9A constructs using lipofectamine reagent (Invitrogen), using standard techniques. Cells stably expressing the hSCN3A or hSCN9A constructs were identified by their resistance to G-418 (400 µg/ml). Clones were screened for expression using the whole-cell voltage-clamp technique.

3.b. Cell Culture

HEK cells stably transfected with hSCN3A or hSCN9A were maintained in DMEM medium supplemented with 10% heat-inactivated fetal bovine serum and 400 µg/ml G418 sulfate in an incubator at 37° C. with a humidified atmosphere of 10% $CO_2$. For HTS, cells were harvested from flasks by trypsinization and replated in an appropriate multi-well plate (typically 96 or 384 wells/plate) such that confluence would be achieved within 24 hours of plating. For electrophysiological studies, cells were removed from the culture flask by brief trypsinization and replated at low density onto glass cover slips. Cells were typically used for electrophysiological experiments within 24 to 72 h after plating.

3.c. Electrophysiological Recording

Cover slips containing HEK cells expressing hSCN3A or hSCN9A were placed in a bath on the stage of an inverted microscope and perfused (approximately 1 ml/min) with extracellular solution of the following composition: 138 mM NaCl, 2 mM $CaCl_2$, 5.4 mM KCl, 1 mM $MgCl_2$, 10 mM glucose, and 10 mM HEPES, pH 7.4, with NaOH. Pipettes were filled with an intracellular solution of the following composition: 135 mM CsF, 5 mM CsCl, 2 mM $MgCl_2$, 10 mM EGTA, 10 mM HEPES, pH 7.3 to 7.4, and had a resistance of 1 to 2 mega ohms. The osmolarity of the extracellular and intracellular solutions was 300 mmol/kg and 295 mmol/kg, respectively. All recordings were made at room temperature (22-24° C.) using AXOPATCH 200B amplifiers and PCLAMP software (Axon Instruments, Burlingame, Calif.) or PatchXpress 7000 hardware and associated software (Axon Instruments, Burlingame, Calif.).

hSCN3A or hSCN9A currents in HEK cells were measured using the whole-cell configuration of the patch-clamp technique (Hamill et al., 1981). Uncompensated series resistance was typically 2 to 5 mega ohms and >85% series resistance compensation (50% for PatchXpress) was routinely achieved. As a result, voltage errors were negligible and no correction was applied. Current records were acquired at 20 to 50 KHz and filtered at 5 to 10 KHz.

HEK cells stably transfected with hSCN3A or hSCN9A were viewed under Hoffman contrast optics and placed in front of an array of flow pipes emitting either control or compound-containing extracellular solutions. All compounds were dissolved in dimethyl sulfoxide to make 10 mM stock solutions, which were then diluted into extracellular solution to attain the final concentrations desired. The final concentration of dimethyl sulfoxide (<0.3% dimethyl sulfoxide) was found to have no significant effect on hSCN3A or hSCN9A sodium currents.

The voltage-dependence of inactivation was determined by applying a series of depolarizing prepulses (8 sec long in 10 mV increments) from a negative holding potential. The voltage was then immediately stepped to 0 mV to assess the magnitude of the sodium current. Currents elicited at 0 mV were plotted as a function of prepulse potential to allow estimation of the voltage midpoint of inactivation ($V_{1/2}$). Cells were then voltage clamped at the empirically determined $V_{1/2}$.

Compounds were tested for their ability to inhibit hSCN3A or hSCN9A sodium channels by activating the channel with a 20 msec voltage step to 0 mV following an 8 second conditioning prepulse to the empirically determined $V_{1/2}$ (Table B). Compound effect (% inhibition) was determined by difference in current amplitude before and after application of test compounds. For ease of comparison, "estimated IC-50" (EIC-50) values were calculated from single point electrophysiology data by the following equation, (tested concentration, uM)×(100-% inhibition/% inhibition). Inhibition values <20% and >80% were excluded from the calculation.

In some cases electrophysiological assays were conducted with PatchXpress 7000 hardware and associated software (Molecular Devices Corp) (Table B). All assay buffers and solutions were identical to those used in conventional whole-cell voltage clamp experiments described above. hSCN3A or hSCN9A containing cells were grown as above to 50%-80% confluency and harvested by trypsinization. Trypsinized cells were washed and resuspended in extracellular buffer at a concentration of $1 \times 10^6$ cells/ml. The onboard liquid handling facility of the PatchXpress was used for dispensing cells and application of test compounds. Determination of the voltage midpoint of inactivation was as described for conventional whole-cell recordings. Cells were then voltage-clamped to the empirically determined $V_{1/2}$ and current was activated by a 20 msec voltage step to 0 mV.

Electrophysiological assays were also conducted using the Ionworks Quattro automated electrophysiological platform (Molecular Devices Corp) (Table C). Intracellular and extracellular solutions were as described above with the following changes, 100 µg/ml amphotericin was added to the intracellular solution to perforate the membrane and allow electrical access to the cells. hSCN3A or hSCN9A containing cells were grown and harvested as for PatchXpress and cells were resuspended in extracellular solution at a concentration of $3-4 \times 10^6$ cells/ml. The onboard liquid handling facility of the Ionworks Quattro was used for dispensing cells and application of test compounds. A voltage protocol was then applied that comprised of a voltage step to fully inactivate the sodium channels, followed by a brief hyperpolarized recovery period to allow partial recovery from inactivation for unblocked sodium channels, followed by a test depolarized voltage step to assess magnitude of inhibition by test compound. Compound effect was determined based on current amplitude difference between the pre-compound addition and post-compound addition scans.

3.d. High-Throughput Screening Assays

Confluent cells in multi-well plates were incubated with a permeant radioactive ion ($^{22}$Na, $^{14}$C-guanidinium, etc) for 4-16 hours to allow uptake of the radiotracer. Excess radioactive ions were removed by washing with prewarmed buffer of the following composition: 138 mM NaCl, 2 mM CaCl$_2$, 5.4 mM KCl, 1 mM MgCl$_2$, 10 mM glucose, and 10 mM HEPES, pH 7.4, with NaOH. Efflux was initiated by addition of buffer containing any necessary chemical activators (e.g., 100 µM veratridine, 10-20 µg/ml Lqh scorpion venom, etc.). Various concentrations of test compounds or reference sodium channel blockers were added concurrently with the initiation of efflux. Efflux was allowed to progress for a defined period of time, typically 30-90 minutes, at 37° C. in a humidified 10% CO$_2$ atmosphere. Stimulated efflux was determined by collecting the extracellular solution and transferring to a multiwell plate for scintillation counting. Residual intracellular radioactivity was also determined by scintillation counting following lysis of the cells in the assay plate. Inhibition of efflux was determined by comparing efflux in the presence of test compounds to efflux in untreated control cells.

The activity of certain compounds of the present invention is set forth in Table III, below.

TABLE III

| Compound | hSCN3A EIC-50 (µM) | hSCN9A EIC-50 (µM) |
|---|---|---|
| N-(thiazol-2-yl)-4-(4-(trifluoromethyl)phenethylsulfonyl)-benzenesulfonamide | 0.16 | >10 |
| 4-(phenylsulfonyl)-N-(thiazol-2-yl)benzenesulfonamide | 5.0 | 2.7 |

While this invention has been disclosed with reference to specific embodiments, it is apparent that other embodiments and variations of this invention may be devised by others skilled in the art without departing from the true spirit and scope of the invention.

All patents, patent applications, and other publications cited in this application are incorporated by reference in their entirety.

What is claimed is:

1. The compound N-thiazol-2-yl)-4-(4-(trifluoromethyl)phenethylsulfonyl)benzenesulfonamide or a pharmaceutically acceptable salt thereof.

2. A pharmaceutical composition comprising the compound of claim 1, or a pharmaceutically acceptable salt thereof, and a pharmaceutically acceptable excipient.

3. A method of modulating activity of a sodium channel in a subject, said method comprising:
administering to said subject in need thereof an effective amount of a compound of claim 1 to modulate the activity of a sodium channel wherein diseases treatable by such modulation of sodium channel activity are selected from pain and seizures.

* * * * *